United States Patent
Gardeski et al.

(10) Patent No.: US 11,197,996 B2
(45) Date of Patent: Dec. 14, 2021

(54) DELIVERY DEVICE FOR DELIVERY OF IMPLANTABLE OR INSERTABLE MEDICAL DEVICES

(71) Applicant: Medtronic, Inc., Minneapolis, MN (US)

(72) Inventors: Kenneth C. Gardeski, Plymouth, MN (US); Ronald A. Drake, St. Louis Park, MN (US); Xin Chen, Blaine, MN (US); Michael R. Leners, St. Francis, MN (US); Lonnie D. Ronning, Coon Rapids, MN (US); Lester O. Stener, Hudson, WI (US); Matthew D. Bonner, Plymouth, MN (US); Jean M. Carver, Blaine, MN (US); Brian P. Colin, Shakopee, MN (US); Alexander R. Mattson, St. Paul, MN (US); Kathryn Hilpisch, Cottage Grove, MN (US); Vladimir Grubac, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 304 days.

(21) Appl. No.: 16/364,309

(22) Filed: Mar. 26, 2019

(65) Prior Publication Data

US 2019/0298989 A1    Oct. 3, 2019

Related U.S. Application Data

(60) Provisional application No. 62/649,277, filed on Mar. 28, 2018.

(51) Int. Cl.
*A61N 1/05* (2006.01)
*A61N 1/365* (2006.01)
(Continued)

(52) U.S. Cl.
CPC ............ *A61N 1/056* (2013.01); *A61B 5/0031* (2013.01); *A61N 1/36585* (2013.01);
(Continued)

(58) Field of Classification Search
CPC .... A61N 1/372; A61N 1/375; A61N 1/37516; A61N 1/057
See application file for complete search history.

(56) References Cited

U.S. PATENT DOCUMENTS

| 2008/9097462 | | 4/2008 | Mitelberg et al. |
| 2011/0276012 | A1* | 11/2011 | Armstrong ........ A61M 25/0043 604/244 |
| 2017/0224997 | A1* | 8/2017 | Shuros ................. A61N 1/3756 |

FOREIGN PATENT DOCUMENTS

EP        2505227 A1    10/2012

OTHER PUBLICATIONS (PCT/US2019/024238) PCT Notification of Transmittal of the International Search Report and the Written Opinion of the International Searching Authority, dated Jun. 6, 2019, 11 pages.

* cited by examiner

*Primary Examiner* — Alyssa M Alter
(74) *Attorney, Agent, or Firm* — Shumaker & Sieffert, P.A.

(57) ABSTRACT

A medical delivery device for delivering a medical device includes a navigable elongated member, a deployment bay, and a compression mechanism. The deployment bay may be configured to house the medical device as the medical device is navigated to the target site. The deployment bay may be at a distal end of the delivery device and may include a distal opening through which the medical device may be deployed. The compression mechanism is configured to longitudinally compress in response to a predetermined
(Continued)

force such that the elongated member and deployment bay are relatively closer together along a longitudinal axis of the delivery device.

35 Claims, 17 Drawing Sheets

(51) Int. Cl.
    *A61B 5/00*           (2006.01)
    *A61N 1/372*        (2006.01)
    *A61N 1/375*        (2006.01)
    *A61B 5/0538*       (2021.01)
    *A61B 5/0215*       (2006.01)
    *A61B 5/283*        (2021.01)

(52) U.S. Cl.
    CPC ........ *A61N 1/37205* (2013.01); *A61B 5/0215* (2013.01); *A61B 5/0538* (2013.01); *A61B 5/283* (2021.01); *A61B 5/686* (2013.01); *A61B 2560/0209* (2013.01); *A61N 1/375* (2013.01); *A61N 1/3756* (2013.01); *A61N 1/37518* (2017.08)

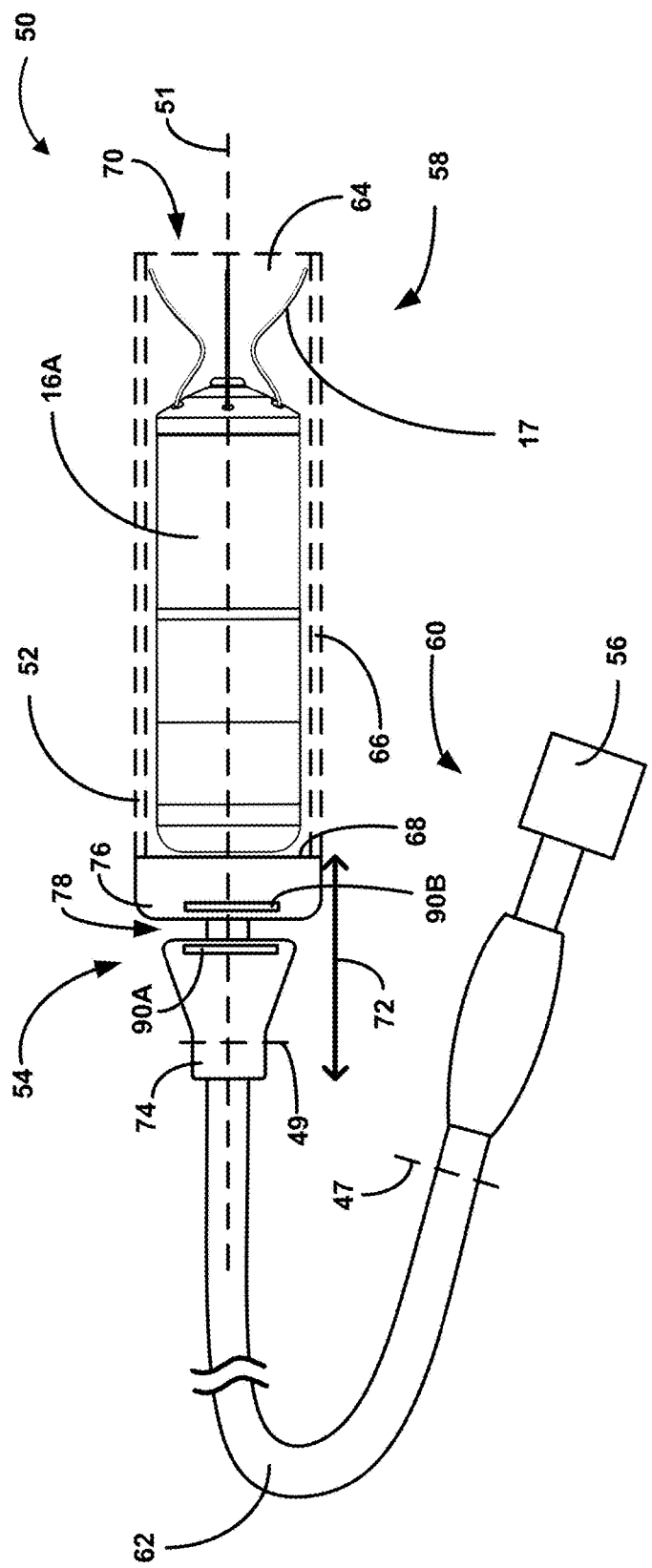

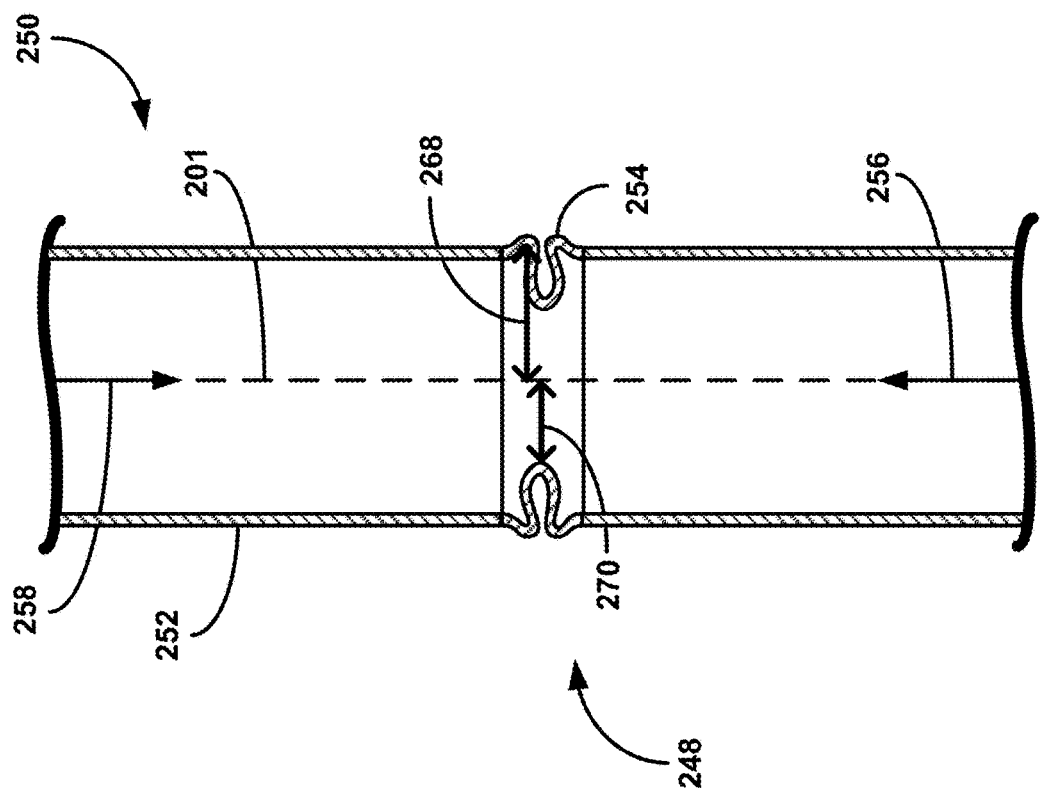
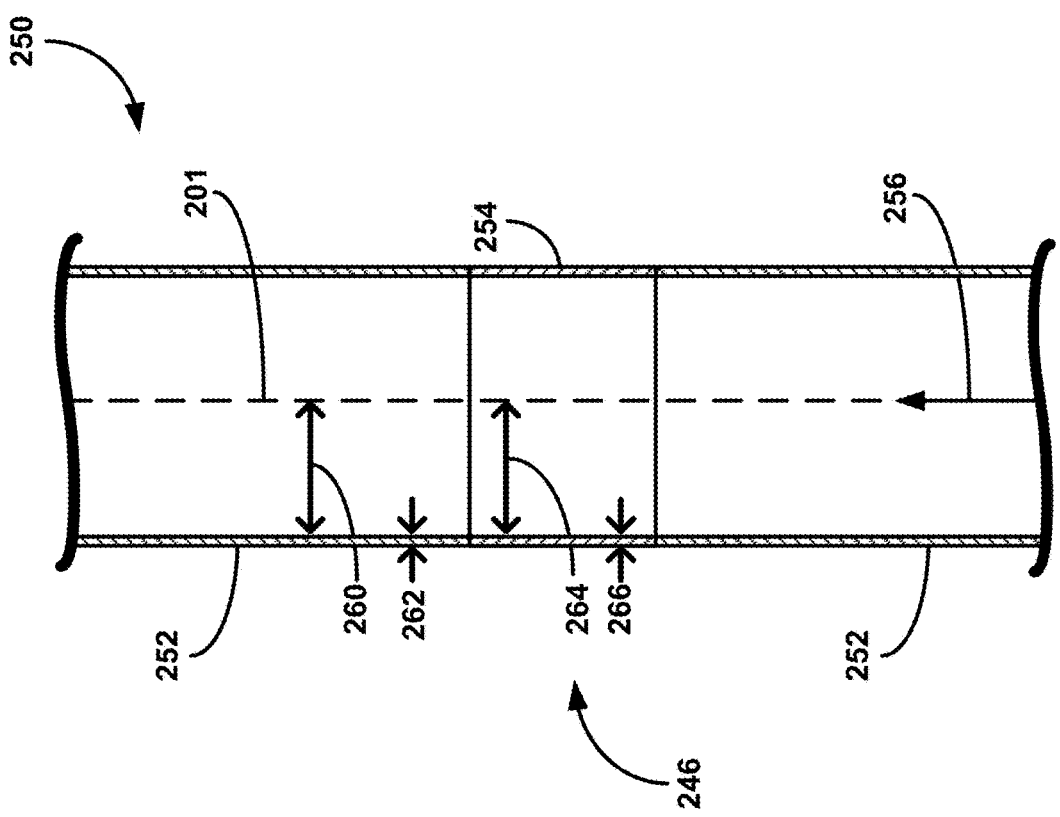

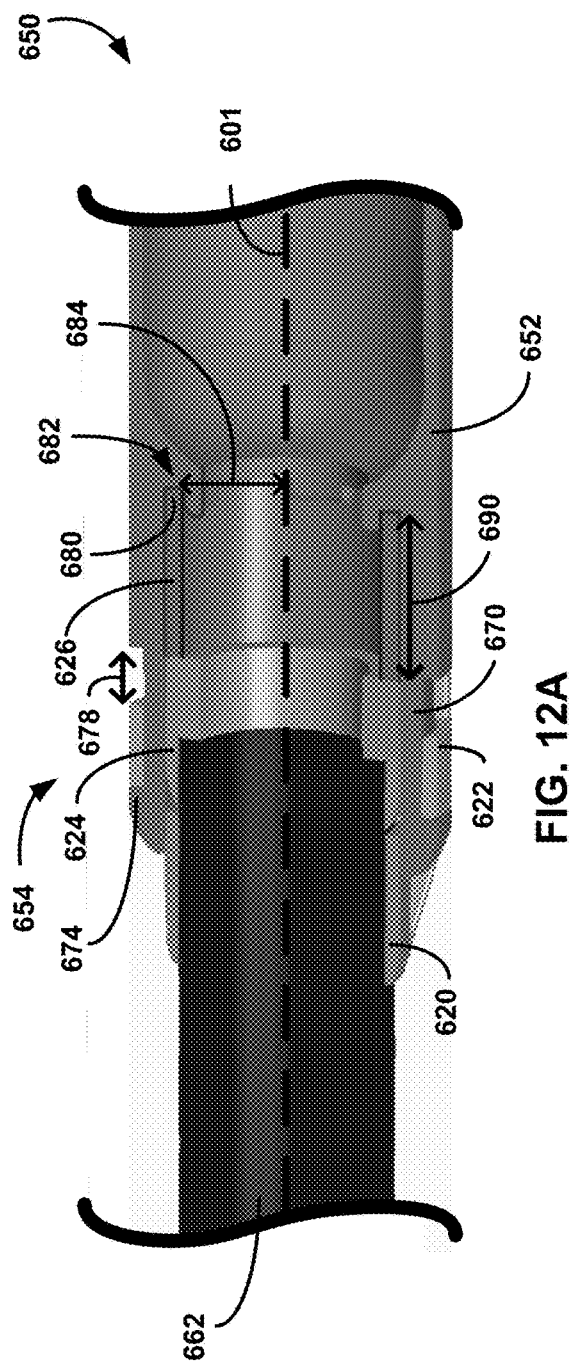
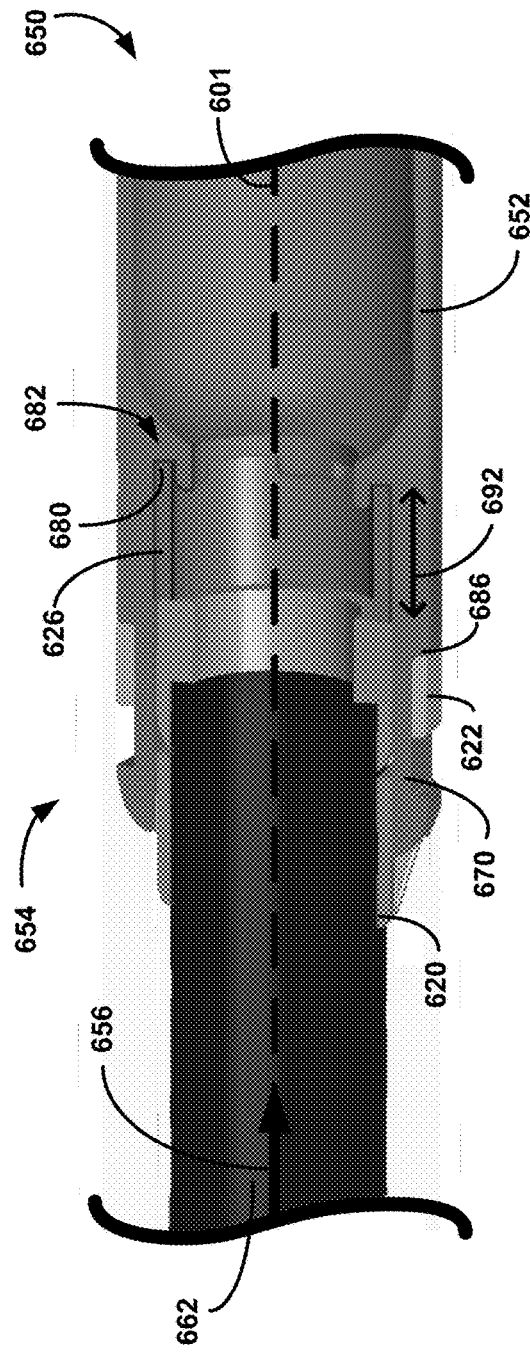
FIG. 12A

DELIVERY DEVICE FOR DELIVERY OF IMPLANTABLE OR INSERTABLE MEDICAL DEVICES

CROSS-REFERENCE TO RELATED APPLICATIONS

This application claims the benefit of U.S. Provisional Application No. 62/649,277, filed Mar. 28, 2018, the entire content of which is incorporated by reference herein.

TECHNICAL FIELD

The disclosure generally relates to medical delivery devices that are configured to deliver implantable and/or insertable medical devices to a target site within a human body.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscles, nerves, brain, stomach or other organs or tissue or a patient. Some medical devices may employ one or more electrodes for the delivery of therapeutic electrical signals to such organs or tissues and/or one or more electrodes for sensing intrinsic electrical signals within the patient that are generated by such organs or tissue. Similarly, some medical devices may additionally or alternatively include one or more other sensors for sensing physiological parameters of a patient.

For example, some medical devices may function as cardiac pacemakers or cardioverter-defibrillators that provide therapeutic electrical signals to the heart. The therapeutic electrical signals may include pulses for pacing, or shocks for cardioversion or defibrillation. In some examples, a medical device may sense intrinsic depolarizations of the heart and thereby control delivery of therapeutic signals to the heart based on the sensed depolarizations. Upon detection of an abnormal rhythm, such as bradycardia, tachycardia, or fibrillation, an appropriate therapeutic electrical signal or signals may be delivered to restore or maintain a predetermined (e.g., relatively more normal) rhythm. For example, in some cases, an implanted medical device may deliver pacing stimulation to the heart of the patient upon detecting tachycardia or bradycardia, and/or deliver cardioversion or defibrillation shocks to the heart upon detecting fibrillation.

In some examples a medical device may utilize one or more medical leads with one or more electrodes or other sensors for delivery of therapeutic electrical signals or sensing. For example, electrodes or sensors may be carried at a distal portion of a lead, where, a proximal portion of the lead may be coupled to a medical device housing that contains circuitry such as signal generation and/or sensing circuitry. Alternatively, an implanted medical device may function without a lead, such that the implantable medical device includes one or more electrodes on its outer housing to deliver therapeutic electrical signals to patient, and/or sense intrinsic electrical signals of patient. For example, leadless cardiac devices, such as leadless pacemakers, may sense intrinsic depolarizations and/or other physiological parameters of the heart and/or deliver therapeutic electrical signals to the heart. Leadless cardiac devices may be positioned within or outside of the heart and, in some examples, may be anchored to a wall of the heart via a fixation mechanism. Leadless cardiac devices may be delivered to the heart percutaneously and/or transvascularly using a device that includes a catheter.

SUMMARY

Aspects of the disclosure are directed to structures of medical delivery devices that are configured to deliver insertable or implantable medical devices to a target site within a human patient. For example, the delivery device may include a navigable elongated member (e.g., a catheter) with a deployment bay, and the insertable or implantable medical device may be an implantable leadless pacemaker. The deployment bay may be configured to house the medical device as the medical device is navigated to the target site. The deployment bay may be at a distal end of the delivery device and may include a distal opening through which the medical device may be deployed. The delivery device may include a compression mechanism that is configured to axially compress (e.g., compress along a longitudinal axis of the delivery device) a predetermined amount in response to a predetermined force such that the elongated member and deployment bay are relatively closer together along a longitudinal axis of the delivery device. In some examples, the compression mechanism is configured to compress in an unbalanced manner such that one longitudinal side of the compression mechanism is relatively more compressed than another longitudinal side (e.g., a longitudinal side on the opposite side of the compression mechanism relative to a longitudinal axis of the delivery device). For example, the compression mechanism may compress in the unbalanced manner in response to the deployment bay contacting the target site at more than a threshold angle. The unbalanced compression may cause the deployment bay to angle relative to the compression mechanism such that a distal face of the deployment bay is flush with the target site.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

FIG. 2A is a conceptual and schematic diagram illustrating an example delivery device that includes an example compression mechanism and a deployment bay that is housing an example implantable medical device.

FIG. 2B is a conceptual and schematic diagram illustrating a cross-sectional view of a first example of the elongated member of the delivery device of FIG. 2A as viewed along one of the cut-planes that intersects the elongated member of FIG. 2A with a deployment mechanism housed by a primary lumen of the elongated member.

FIG. 2C is a conceptual and schematic diagram illustrating a cross-sectional view of a second example of the elongated member of the delivery device of FIG. 2A as viewed along one of the cut-planes that intersects the elongated member of FIG. 2A with a deployment mechanism housed by a dedicated deployment mechanism lumen of the elongated member.

FIG. 2D is a conceptual and schematic diagram illustrating a cross-sectional view of the compression mechanism of the delivery device of FIG. 2A as viewed along one of the cut-planes that intersects the compression mechanism of FIG. 2A.

FIGS. 7A and 7B are conceptual and schematic diagrams illustrating cross-sectional views of an uncompressed and compressed state, respectively, of an example delivery device that includes an example compression mechanism with relatively differently physical properties in relation to adjacent portions of the delivery device.

FIGS. 12A and 12B are conceptual and schematic diagram illustrating a cross-sectional view of the compression mechanism of delivery device of FIGS. 11A and 11B as viewed along a cut-plane taken along the longitudinal axis of FIGS. 11A and 11B in an uncompressed state and a compressed state, respectively.

DETAILED DESCRIPTION

Figure 1A:
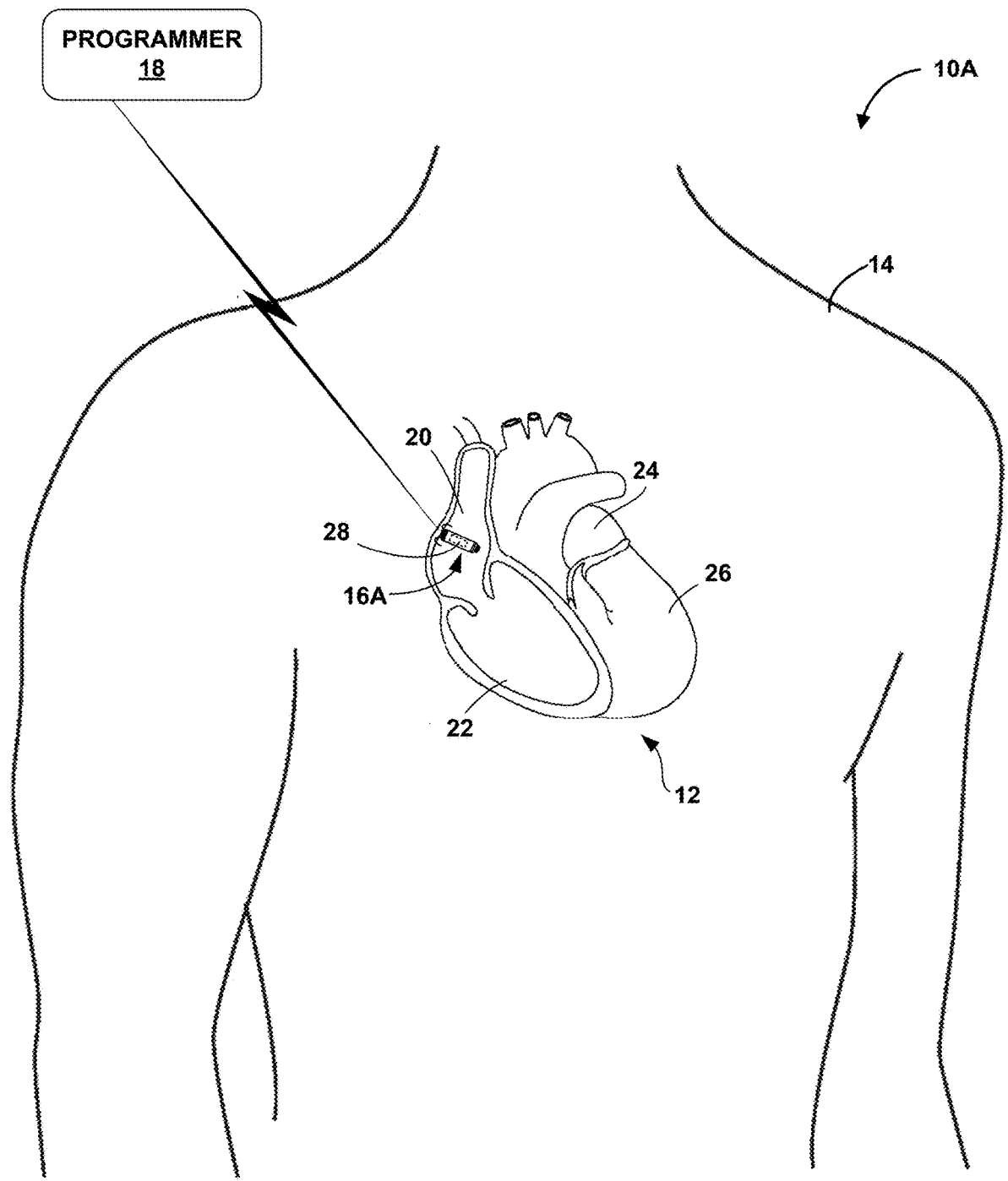
FIG. 1A is a conceptual and schematic diagram illustrating an example therapy system comprising a leadless implantable medical device that may be used to monitor one or more physiological parameters of a patient and/or provide therapy to the heart of a patient.

Aspects of this disclosure relate to methods and systems for delivering an insertable or implantable medical device to a target site in a patient. The medical device may be secured to the target site once navigated to the target site with fixation elements on or near a distal end of the medical device. The delivery device may include a proximal hub, a navigable elongated member (e.g., a catheter) extending from the hub, a deployment bay at a distal end of the elongated member, and a compression mechanism.

The compression mechanism may extend around a full outer perimeter or circumference of the delivery device along an axial length of the delivery device. The compression mechanism may be configured to axially compress (e.g., compress along a longitudinal axis of the delivery device) relative to other portions of the delivery device, such that other portions of the delivery device define a substantially constant axial length in response to the predetermined force while an overall axial length of the delivery device compresses an amount that corresponds to the compression of the compression mechanism. Put differently, the compression mechanism may define a first axial length as measured along a longitudinal axis of the delivery device between a proximal portion and distal portion of the compression mechanism which is reduced to a second, shorter axial length in response to the compression mechanism compressing in response to the predetermined force.

In some examples it may be advantageous to verify that the deployment bay is pressed against the target site with a predetermined amount of force before deploying the medical delivery device. For example, deploying the medical device upon initial contact may result in a fixation mechanism of the medical device loosely or otherwise sub-optimally securing itself to the tissue layer of the target site. Loosely securing the medical device to the target site may increase a likelihood of electrodes or sensors of the medical device achieving poor contact or positions, and therein having difficulty providing therapy to and/or monitoring the patient, or becoming unsecured within the patient. Similarly, deploying the medical device subsequent to pressing the deployment bay against the target site with relatively too high of a force may result in the medical device securing itself to sensitive muscle tissue of the patient that is beyond the targeted tissue layer of the target site (e.g., beyond as from the vantage point of the medical device). Aspects of this disclosure may improve an ability of a delivery device to provide feedback to a clinician in response to the deployment bay pressing against the target site with a predetermined (e.g., desired) amount of force (or a force within a desired and/or predetermined range of forces) by compressing a predetermined amount in response to the predetermined force.

A delivery device that is navigated to a target site in a patient may be introduced to the patient's body, e.g., percutaneously, using an introducer sheath that provides a breechable seal into the intravenous system of the patient. In some examples, this seal may constantly press radially in toward a center of the seal to maintain the seal. Breeching this seal to insert the delivery device through the introducer sheath may require an amount of force. The amount of force required to insert the delivery device may be less than the threshold force required to compress the delivery device via the compression mechanism, such that the compression mechanism may avoid causing the delivery device to compress or otherwise deform during insertion of the delivery device. It may be advantageous for the delivery device to define a relatively static profile during insertion to provide predictable feedback to a clinician performing the insertion.

Following insertion, the delivery device may be removed through the same introducer sheath, while the medical device is left inserted or implanted within the patient as secured to the target site. In some examples, the compression mechanism may be located immediately proximal to the deployment bay. Further, in some examples as discussed and depicted herein, the compression mechanism may provide a relatively smooth or gradual transition from the relatively smaller radius of the elongated member to the relatively greater radius of the deployment bay. Providing such a smooth transition may reduce a difficulty of rebreeching the seal of the introducer sheath when removing the deployment bay from the patient using the introducer sheath.

FIG. 1A is a conceptual diagram illustrating an example therapy system 10A that may be used to monitor one or more physiological parameters of heart 12 of patient 14 and/or to provide therapy to heart 12 of patient 14 using one or more medical devices delivered using the delivery device of this disclosure. Therapy system 10A includes implantable medical device (IMD) 16A, which is communicatively coupled, e.g., wirelessly, to external device 18. IMD 16A may be an implantable leadless pacemaker that provides electrical signals to heart 12 via one or more electrodes (not shown in FIG. 1) on its outer housing. Additionally, or alternatively, IMD 16A may sense electrical signals attendant to the depolarization and repolarization of heart 12 via electrodes on its outer housing. In some examples, IMD 16A provides pacing pulses to heart 12 based on the electrical signals sensed within heart 12. For example, IMD 16A may be a Micra™ device of the Transcatheter Pacing System (TPS), which is commercial available from Medtronic Public Limited Company.

For example, IMD 16A may include internal circuitry 28. IMD 16A may define a housing that is hermetically sealed within which IMD 16A contains internal circuitry 28. IMD 16A may also include a power source and/or memory to for internal circuitry 28. Internal circuitry 28 may be configured to provide the functionality attributed to implantable medical devices herein. Internal circuitry 28 may include one or more microprocessors, digital signal processors (DSPs), application specific integrated circuits (ASICs), field programmable gate arrays (FPGAs), or any other equivalent integrated or discrete logic circuitry, as well as any combinations of such components.

For example, internal circuitry 28 may include processing circuitry, stimulation circuitry, telemetry circuitry, sensing circuitry, or the like. Stimulation circuitry may generate and deliver electrical stimulation under the control of processing circuitry. For example, in operation, processing circuitry may access a memory to load therapy programs to stimulation circuitry, where stimulation parameters of therapy programs may include a voltage amplitude, a current amplitude, a pulse rate, a pulse width, a duty cycle, or a combination of electrodes (e.g., where electrodes are secured to IMD 16A). Telemetry circuit may be configured for wireless communication using radio frequency protocols or inductive communication protocols. Telemetry circuit may include one or more antennas configured to communicate with external device 18, for example. Processing circuit may transmit operational information such as sensing information and receive therapy programs or therapy parameter adjustments via telemetry circuit. Also, in some examples, IMD 16A may communicate with other implanted devices, such as stimulators, control devices, or sensors, via telemetry circuit. Sensing circuitry may be configured to sense one or more parameters of patient 14. For example, sensing circuitry may sense parameters of heart 12 using electrodes of IMD 16A. Based on sensed values of sensing circuitry, processing circuitry may use telemetry circuitry to provide information or use stimulation circuitry to provide therapy related to sensed values.

IMD 16A may include fixation elements such as a set of fixation tines to secure IMD 16A to a patient tissue. The fixation elements of IMD 16A may be located near a distal end of IMD 16A, such that the fixation elements are configured to extend out the distal opening of the deployment bay of the delivery device substantially immediately upon IMD 16A being deployed using the delivery device. In the example of FIG. 1, IMD 16A is positioned wholly within heart 12 proximate to an inner wall of right atrium 20 to provide right atrium 20 pacing. Although IMD 16A is shown within heart 12 and proximate to an inner wall of right atrium 20 in the example of FIG. 1, IMD 16A may be positioned at any other location outside or within heart 12. For example, IMD 16A may be positioned outside or within right ventricle 22, left atrium 24, and/or left ventricle 26, e.g., to provide right ventricle, left atrial, and left ventricular pacing, respectively. Further, although a single IMD 16A is shown in FIG. 1A, system 10A may include additional IMDs that are similar to or different from IMD 16A.

Depending on the location of implant, IMD 16A may include other stimulation functionalities. For example, IMD 16A may provide atrioventricular nodal stimulation, fat pad stimulation, vagal stimulation, or other types of cardiac stimulation or neurostimulation. In other examples, IMD 16A may be a monitor that senses one or more parameters of heart 12, e.g., electrical activity mechanical activity, and/or pressure, and may not provide any stimulation functionality. In some examples, system 10A may include a plurality of leadless IMDs 16A to provide stimulation and/or sensing at a variety of locations. IMD 16A may include distal fixation elements such as a set of fixation tines.

As mentioned above, IMD 16A may be delivered and deployed to its target site using the delivery device described herein. IMD 16A may be contained substantially entirely within a deployment bay of the delivery device such that fixation elements of IMD 16A are adjacent a distal opening of the deployment bay. Upon securing attachment of IMD 16A to the target site (e.g., through fixation tines as depicted in FIG. 1A), delivery device may be retracted from patient 14 (e.g., including retracting the delivery device of over a proximal end of IMD 16A, depending upon whether IMD 16A may be secured before full deployment).

FIG. 1A further depicts external device 18 such as a (clinician or patient) programmer in wireless communication with IMD 16A. In some examples, external device 18 comprises a handheld computing device, computer workstation, or networked computing device. External device 18 may include a user interface that presents information to and receives input from a user. It should be noted that the user may also interact with external device 18 remotely via a networked computing device.

A user, such as a physician, technician, surgeon, electrophysiologist, other clinician, or patient, interacts with external device 18 to communicate with IMD 16A. For example, the user may interact with external device 18 to retrieve physiological or diagnostic information from IMD 16A. For example, the user may use external device 18 to retrieve information from IMD 16A regarding the rhythm of heart 12, heart rhythm trends over time, or arrhythmic episodes. A user may also interact with external device 18 to program IMD 16A.

In some examples, the user may use external device 18 to retrieve information from IMD 16A regarding other sensed physiological parameters of patient 14 or identify information that is derived from sensed physiological parameters, such as intracardiac or intravascular pressure, activity, posture, tissue oxygen levels, blood oxygen levels, respiration, tissue perfusion, heart sounds, cardiac electrogram (EGM), intracardiac impedance, thoracic impedance, or the like. In some examples, the user may use external device 18 to retrieve information from IMD 16A regarding the performance or integrity of IMD 16A or the performance or integrity of respective components of system 10A, such as a power source of IMD 16A. As another example, the user may interact with external device 18 to select values of parameters of therapies provided by IMD 16A, such as pacing and/or neurostimulation therapies.

IMD 16A and external device 18 may communicate via wireless communication using any techniques known in the art. Examples of communication techniques may include, for example, low frequency or radiofrequency (RF) telemetry. In some examples, external device 18 may include a programming head that may be placed proximate to the patient's body near the IMD 16A implant site in order to improve the quality or security of communication between IMD 16A and external device 18.

Figure 1B:
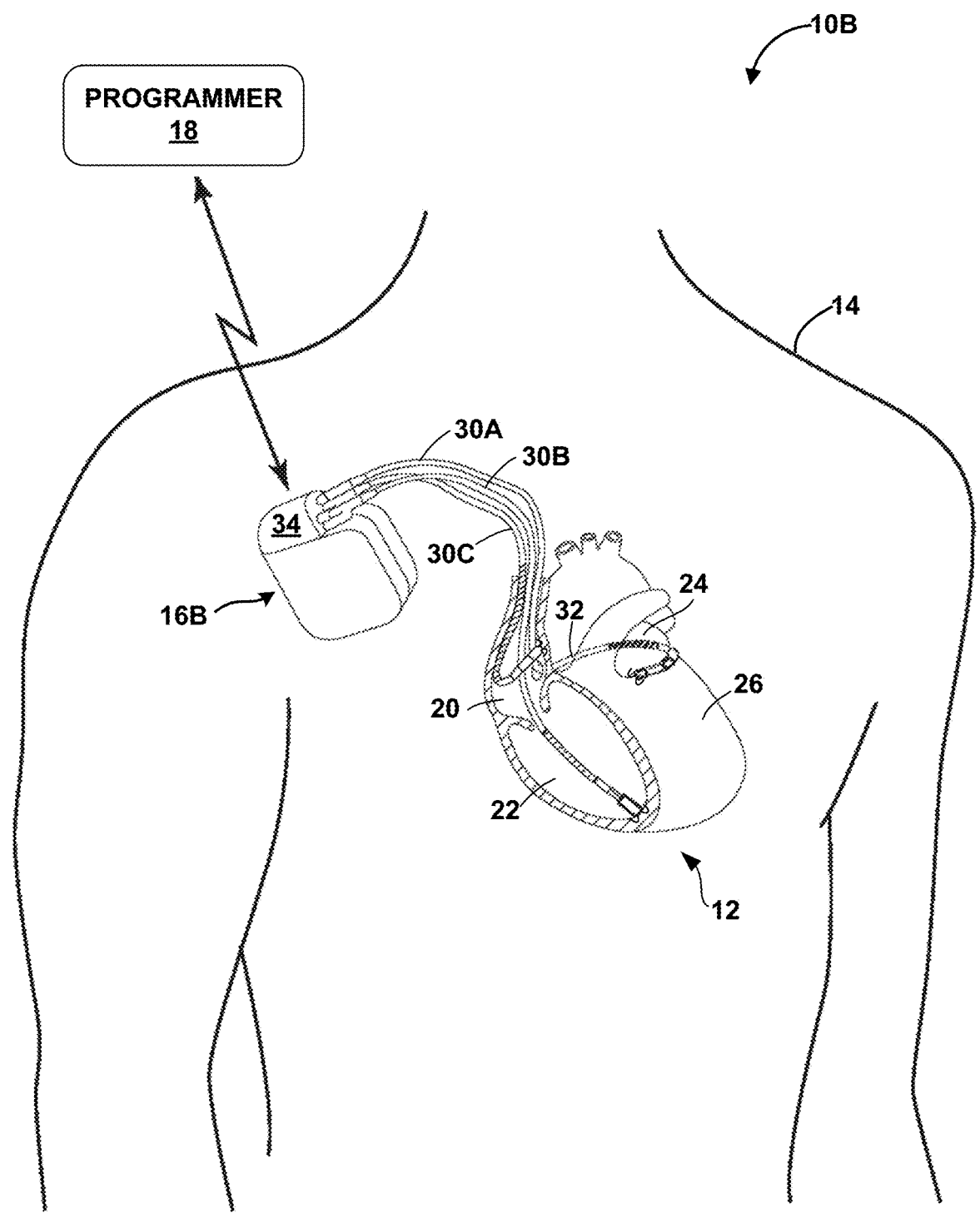
FIG. 1B is a conceptual and schematic diagram illustrating another example therapy system comprising an implantable medical device coupled to a plurality of leads that may be used to monitor one or more physiological parameters of a patient and/or provide therapy to the heart of a patient.

FIG. 1B is a conceptual diagram illustrating another example therapy system 10B that may be used to monitor one or more physiological parameters of patient 14 and/or to provide therapy to heart 12 of patient 14 using medical device inserted or implanted using the delivery device described herein. Therapy system 10B includes IMD 16B, which is coupled to medical leads 30A, 30B, 30C (collectively "leads 30") and external device 18. As referred to herein, each of IMD 16B and medical leads 30 may be referred to generally as an IMD. In one example, IMD 16B may be an implantable pacemaker that provides electrical signals to heart 12 via electrodes coupled to one or more of leads 30. IMD 16B may include an electrical stimulation generator and may be attached to the proximal end of medical leads 30. In other examples, in addition to or alternatively to pacing therapy, IMD 16B may deliver neurostimulation signals. In some examples, IMD 16B may also include cardioversion and/or defibrillation functionalities. In other examples, IMD 16B may exclusively or predominantly provide monitoring functionalities. Patient 14 is ordinarily, but not necessarily, a human patient.

Medical leads 30 extend into the heart 12 of patient 14 to sense electrical activity of heart 12 and/or deliver electrical stimulation to heart 12. In some examples, each medical lead 30 of FIG. 1B may be delivered to their respective target sites using the delivery device described herein. In the example shown in FIG. 1B, right ventricular (RV) lead 30B extends through one or more veins (not shown), the superior vena cava (not shown), right atrium 20, and into right ventricle 22. RV lead 30B may be used to deliver RV pacing to heart 12. Left ventricular (LV) lead 30A extends through one or more veins, the vena cava, right atrium 20, and into the coronary sinus 32 to a region adjacent to the free wall of left ventricle 26 of heart 12. Alternatively, LV lead 30A may be implanted "directly" into the left ventricle 26, such that LV lead 30A, e.g., extends through a hole in the ventricular septum or atrial septum. LV lead 30A may be used to deliver LV pacing to heart 12. Right atrial (RA) lead 30C extends through one or more veins and the vena cava, and into the right atrium 20 of heart 12. RA lead 30C may be used to deliver RA pacing to heart 12.

In some examples, system 10B may additionally or alternatively include one or more leads or lead segments (not shown in FIG. 1B) that deploy one or more electrodes within the vena cava or other vein, or within or near the aorta. Furthermore, in another example, system 10B may additionally or alternatively include one or more additional intravenous or extravascular leads or lead segments that deploy one or more electrodes epicardially, such as near an epicardial fat pad, or proximate to the vagus nerve. In other examples, system 10B may not include one of ventricular leads 30A and 30B.

One or more of medical leads 30 may include fixation elements such as a set of fixation tines to secure a distal end of the medical lead to a patient tissue. The inclusion of fixation elements such as tines for each medical lead 30 is merely illustrated for purposes of clarity. As depicted, fixation elements may include distal tines that are configured to distally extend from leads 30 and are self-biasing upon deployment (e.g., deployed from a deployment bay of a delivery device as described herein to a biased configuration). In other examples, fixation elements may include other types of tines, such as tines that do not self-bias (but are caused to bias or deform or actuate by another component), tines of other shapes (e.g., helical tines), tines that are configured to be manually controlled to a clinician, or the like. Fixation elements such as tines may be constructed of substantially any bio-compatible material. In some examples, one of the medical leads 30 may be secured by alternative techniques than are used to secure the respective other medical leads 30. For example, even though each of medical leads 30 is shown as secured with a set of fixation tines, LV lead 30A, which extends through one or more veins and the vena cava and into the right atrium 20 of heart 12, may instead be secured to heart 12 using an alternate technique such as "passive fixation" (e.g., such that LV lead 30A is secured to the target site without means to holds the end of LV lead 30A against the target site, but rather is held against the target site by a pressure generated by a shape and longitudinal tension of LV lead 30A).

As mentioned above, one or more medical leads 30 may be delivered and deployed to respective target sites using the delivery device described herein. Medical leads 30 may be deployed to respective target sites within or near heart 12 in subsequent procedures using one or more the delivery devices herein. In such examples, the fixation elements of the respective medical leads 30 may be navigated to the target site within a deployment bay of the delivery device, such that other portions of respective medical leads 30 may be housed by a lumen of some of the deployment bay, compression mechanism, and/or elongated member. Upon deploying the distal end of medical leads 30 to secure respective medical leads 30 to the target site, the delivery device may be withdrawn over respective medical leads 30 to retract the delivery device from patient 14. In this way, upon successfully deploying one of medical leads 30, a clinician may retract the delivery device such that the delivery device moves proximally relative to the respective deployed medical lead 30 (e.g., such that respective deployed and distally secured medical lead 30 slides within the one or more lumens of the delivery device as defined by the deployment bay, compression mechanism, and/or elongated member of the delivery device as the delivery device is retracted).

IMD 16B may sense electrical signals attendant to the depolarization and repolarization of heart 12 via electrodes coupled to at least one of the leads 30. In some examples, IMD 16B provides pacing pulses to heart 12 based on the electrical signals sensed within heart 12. The configurations of electrodes used by IMD 16B for sensing and pacing may be unipolar or bipolar.

IMD 16B may also provide neurostimulation therapy, defibrillation therapy and/or cardioversion therapy via electrodes located on at least one of the leads 30. For example, IMD 16B may deliver defibrillation therapy to heart 12 in the form of electrical pulses upon detecting ventricular fibrillation of ventricles 22 and 26. In some examples, IMD 16B may be programmed to deliver a progression of therapies, such as pulses with increasing energy levels, until a fibrillation of heart 12 is stopped. As another example, IMD 16B may deliver cardioversion or anti-tachycardia pacing (ATP) in response to detecting ventricular tachycardia, such as tachycardia of ventricles 22 and 26.

As described above with respect to IMD 16A of FIG. 1, external device 18 such as a clinician or patient programmer may be used to communicate with IMD 16B. In addition to the functions described with respect to IMD 16A of FIG. 1, a user may use external device 18 to retrieve information from IMD 16B regarding the performance or integrity of leads 30 and may interact with external device 18 to select parameters for any additional therapies provided by IMD 16B, such as cardioversion and/or defibrillation.

Leads 30 may be electrically coupled to signal generation circuitry and sensing circuitry (not shown) of IMD 16B via connector block 34. In some examples, proximal ends of leads 30 may include electrical contacts that electrically couple to respective electrical contacts within connector block 34 of IMD 16B. Although not shown in FIG. 1B, IMD 16B may include circuitry 28, similar to IMD 16A. Circuitry 28 may include the processing circuitry, signal generation circuitry, and sensing circuitry described above, along with any other circuitry, power source, antennas, or other hardware or software necessary or helpful to configure IMD 16B to provide therapy and/or monitor a condition of patient 14.

The configuration of system 10B illustrated in FIG. 1B is merely one example. In other examples, a system may include extravascular leads, subcutaneous lead, substernal leads, epicardial leads and/or patch electrodes instead of or in addition to the transvenous leads 30 illustrated in FIG. 1B. Further, IMD 16B need not be implanted within patient 14. For each of these examples, any number of the medical leads may include a set of fixation tines on a distal end of the medical lead that were navigated to their respective target sites using delivery devices in accordance with the techniques described herein.

In addition, in other examples, a system may include any suitable number of leads coupled to IMD 16B, and each of the leads may extend to any location within or proximate to heart 12. For example, other examples of systems may include three transvenous leads located as illustrated in FIG. 1B, and an additional lead located within or proximate to left atrium 24. Other examples of systems may include a single lead that extends from IMD 16B into right atrium 20 or right ventricle 22, or two leads that extend into a respective one of the right ventricle 22 and right atrium 20. In each of these examples, any number of the medical leads may include a fixation mechanism on a distal end of the medical lead and may be delivered with a medical delivery device in accordance with the techniques described herein.

FIG. 2A depicts an example medical delivery device 50 for delivering an insertable or implantable medical device, e.g., IMD 16B or, as illustrated in FIG. 2A, IMD 16A. FIG. 2A depicts cross-sectional cut-plane 47 of cross-sectional view of FIGS. 2B and 2C (where FIGS. 2B and 2C depict two examples of a cross-sectional construction of delivery device 50), cut-plane 49 of cross-sectional view of FIG. 2D, and cut-plane 51 of cross-sectional view of FIG. 3. Delivery device 50 may include deployment bay 52 that is configured to house at least a portion of the medical device and deploy the medical device. In some examples, deployment bay 52 may be configured to house substantially all of the insertable or implantable medical device prior to deploying the medical device.

Delivery device 50 may further include compression mechanism 54 that axially deforms (e.g., deforms along a longitudinal axis of the delivery device) in response to an axial force above a threshold force. Delivery device 50 may further include hub 56 for handling delivery device 50. In some examples, hub 56 may be configured to remain external to patient 14 as deployment bay 52 is navigated to the target site, enabling a clinician to navigate an intravenous system and deploy a medical device using one or more mechanisms or ports (not depicted) of hub 56. Deployment bay 52 may be located at or near distal end 58 of delivery device 50, and hub 56 may be located at or near proximal end 60 of delivery device 50, with elongated member 62 extending between hub 56 and deployment bay 52, each of which are discussed in detail below.

Elongated member 62 may be a flexible elongated cylindrical component, although member 62 may define one or more other cross-section shapes, including defining a plurality of cross-sectional shapes along a longitudinal length of elongated member 62. Elongated member 62 may define a number of internal longitudinal lumens for a variety of purposes. For example, as depicted in conceptual and schematic cross-sectional view of FIG. 2B, elongated member 62 may define primary lumen 80 that occupies a majority of a cross-sectional width of elongated member 62.

Primary lumen 80 may be configured to house deployment mechanism 86A that can axially slide (e.g., slides along a longitudinal axis of the delivery device) within primary lumen 80 relative to delivery device 50 (e.g., such that an insertable or implantable medical device that is navigated to the target site by delivery device 50 may be deployed from deployment bay 52 as a result of an action executed using deployment mechanism 86A). For example, deployment mechanism 86A may be some form of a tether or catch that is used to hold, push, or otherwise move an inserted or implanted medical device in order to deploy the medical device from deployment bay 52. Alternatively, or additionally, primary lumen 80 may be configured to house a portion of an insertable or implantable medical device to be deployed by delivery device 50 as described herein. Elongated member 62 may further define guidewire lumen 82 that is configured to house a guidewire that can axially slide (e.g., compress along a longitudinal axis of the delivery device) within the guidewire lumen relative to delivery device (e.g., such that deployment bay 52 is navigated to the target site by sliding delivery device along a guidewire that was previously navigate to the target site). Alternatively, or additionally, one or more deflection members 84 may be embedded within elongated member 62 that are used to deflect elongated member 62 in one or more directions. For example, deflection members 84 may include wires that are pulled from a port (not depicted) on hub 56 to deflect elongated member 62. Deflection members 84 may be configured to deflect elongated member 62 in a predetermined manner that is configured to navigate delivery device 50 to the target site. Put differently, deflection members 84 as longitudinally embedded within elongated member 62 may be configured to deflect elongated member 62 in a predetermined manner when delivery device 50 is inserted in patient 14 (e.g., to navigate through a particularly tortuous and predetermined length of intravenous system).

In some examples, elongated member 62 may include a different combination of lumens and/or longitudinal elements, whether for similar or different purposes. For example, FIG. 2C depicts a conceptual and schematic diagram of a second example cross-sectional construction of elongated member 62. The cross-sectional construction of elongated member 62 as depicted in FIG. 2C is substantially similar to the cross-sectional construction of elongated member 62, with the exception that elongated member 62 of FIG. 2C defines a dedicated deployment lumen 88 that is configured to house deployment mechanism 86B. Deployment mechanism 86B may be substantially similar to deployment mechanism 86A, in that deployment mechanism 86B may be configured to axially slide within deployment lumen 88 relative to delivery device and deploy the medical device once deployment bay 52 is adjacent the target site.

Turning back to FIG. 2A, delivery device 50 may be configured to be inserted into patient 14 to deliver an insertable or implantable medical device. Delivery device 50 may be configured to be inserted into patient 14 using an introducer sheath (not depicted). In some examples, delivery device 50 may include entirely biocompatible materials. For example, delivery device 50 may include polymer materials such as polyether block amide (PEBA), low density polyethylene (LDPE), high density polyethylene (HDPE), polytetrafluoroethylene (PTFE), polybutylene terephthalate (PBT), polyethylene terephthalate (PET), nylons, or the like, and/or metal materials such as titanium, nitinol, stainless steel, or the like. Delivery device 50 may be configured such that a clinician inserting deployment bay 52 into patient 14 and navigating deployment bay 52 to a target site within patient 14 may not result in a force above a threshold force for deformation of compression mechanism 54 being applied to compression mechanism 54 (e.g., such that compression mechanism 54 substantially resists deforming as discussed herein in response to either insertion or navigation to the target site).

In some examples, as depicted in FIG. 2A, deployment bay 52 may house the insertable or implantable medical device to be deployed, such that the deployment bay 52 is configured to fit most or substantially all of the respective insertable or implantable medical device within recess 64 defined by deployment bay 52. For example, as depicted in FIG. 2A, deployment bay 52 may house IMD 16A within recess 64 as defined by outer wall 66 of deployment bay 52 and proximal wall 68 defined by deployment bay 52. Outer wall 66 may be configured to radially enclose an axial length of a medical device such as IMD 16A. Further proximal wall 68 may be configured to block proximal movement of a medical device such as IMD 16A relative to deployment bay 52. Though deployment bay 52 is depicted as transparent in FIG. 2A for purposes of illustration (to depict IMD 16A), it is to be understood that deployment bay 52 may define a substantially contiguous enclosure for the respective medical device to be delivered by delivery device 50.

Deployment bay 52 may further define distal opening 70 to recess 64 through which IMD 16A may be deployed from recess 64. In some examples, a distal-most surface of deployment bay 52 may define distal opening 70. Deployment bay 52 may define recess 64 as a physical space that is sized to partially or entirely contain a medical device such as IMD 16A as delivery device 50 is navigated into patient 14 to deliver the respective medical device. Deployment bay 52 may define recess 64 such that, when IMD 16A is received within recess 64, fixation element 17 is proximal to distal opening 70. In some examples, one or more fixation elements 17 may be interfacing with an inner circumference of deployment bay 52 in advance of deployment from deployment bay 52. As discussed herein, compression mechanism 54 may be configured to improve an ability of fixation elements 17 to secure to tissue at a target site. For example, compression mechanism 54 may improve an ability of fixation elements to deploy and/or provide a force in distal direction 92 and/or radial direction 94 as depicted in FIG. 2A. Improving an ability of fixation elements 17 deploying and/or providing a force in distal direction 92 may improve an ability of IMD 16A securing to right ventricle 22. Alternatively, improving an ability of fixation elements 17 deploying or providing a force in radial direction 94 may improve an ability of IMD 16A to secure to right atrium 20.

In certain examples (not depicted), deployment bay 52 may alternatively or additionally be configured to deploy an insertable or implantable medical device that extends through a length of delivery device 50. For example, delivery device 50 may be configured to deliver one or more leads 30 of IMD 16B.

As depicted in conceptual and schematic cross-sectional view of FIG. 2D, compression mechanism 54 may define elongated member lumen 81 through which elongated member 62 may axially extend that occupies a majority of a cross-sectional width of compression mechanism 54. As depicted in FIG. 2D, elongated member 62 defines a similar cross-sectional construction as depicted FIG. 2B (e.g., rather than as depicted in FIG. 2C), but in other examples elongated member 62 may define other lumens or include other features than those lumens and features depicted in FIG. 2D. In some examples, deployment bay 52 may define a hole within proximal wall 68 (or may not define proximal wall at all). A deployment mechanism such as deployment mechanism 86A may extend through such a hole to initially retain and subsequently deploy the medical device as housed within deployment bay 52. Alternatively, the insertable or implantable medical device may include a lead such as lead 30 (of FIG. 1B) that may extend through a hole in proximal wall 68 from elongated member 62 to deployment bay 52, such that a distal fixation element of lead 30 may be proximate to distal opening 70 of deployment bay 52.

As depicted in FIG. 2D, elongated member 62 may no longer include embedded deflection member 84 at a longitudinal location at which elongated member 62 is within elongated member lumen 81 of compression mechanism 54. Put differently, compression mechanism 54 may be longitudinally located along delivery device 50 at a location distal to the distal end of deflection member 84. As discussed herein, deflection member 84 may be deflected to deform elongated member 62 in a predetermined manner. In some examples, elongated member 62 may be configured to be relatively longitudinally consistent along a length of elongated member 62, such that elongated member 62 defines a relatively static cross-sectional shape as made of a relatively static set of materials. Configuring elongated member 62 to be relatively longitudinally consistent in this manner may improve an ability of deflection member 84 to deform elongated member 62 in this predetermined manner, as a longitudinally consistent component may introduce less factors to be accounted for. Similarly, locating compression mechanism 54 on delivery device 50 at a location that is distal to deflection member 84 may simplify a deflection procedure for deflection member 84 and therein improve an ability for deflection member 84 to deflect elongated member 62 according to the predetermined manner (e.g., as locating compression mechanism 54 distal to deflection member 84 may reduce the number of variables that need to be correctly accounted for during a deflection procedure as compression mechanism 54 may have a relatively different reaction to the deflection/deformation of deflection member 84 than the consistent longitudinal profile of elongated member 62). Improving an ability for deflection member 84 to deflect according to the predetermined (e.g., desired) manner may improve an ability for delivery device 50 to deliver a medical device to the target site of a patient.

Figure 4A:
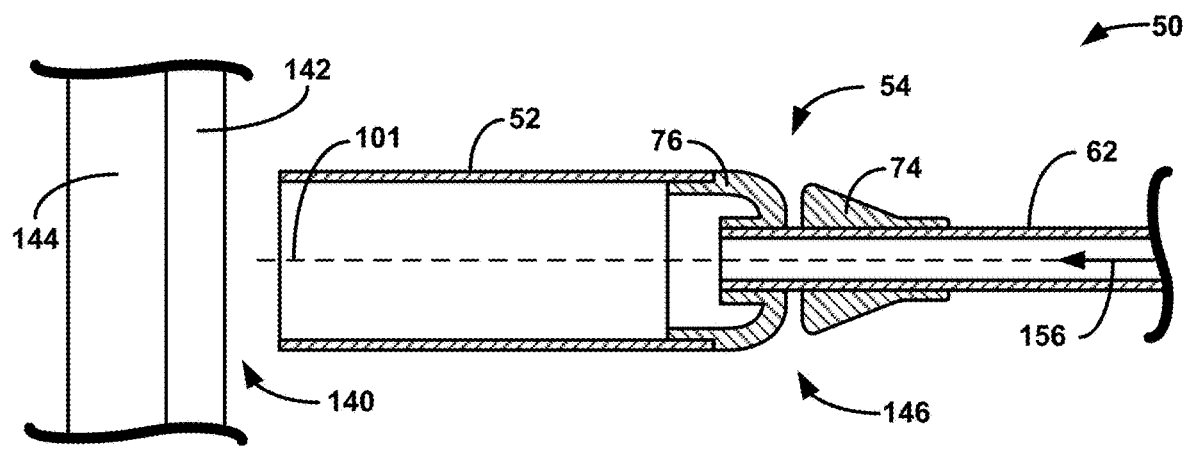
FIGS. 4A-4C are conceptual and schematic diagrams illustrating cross-sectional views of the delivery device of FIG. 2A as viewed along one of the cut-planes of FIG. 2A as the delivery device approaches, contacts, and presses against, respectively, a target site in a patient.
Figure 4B:
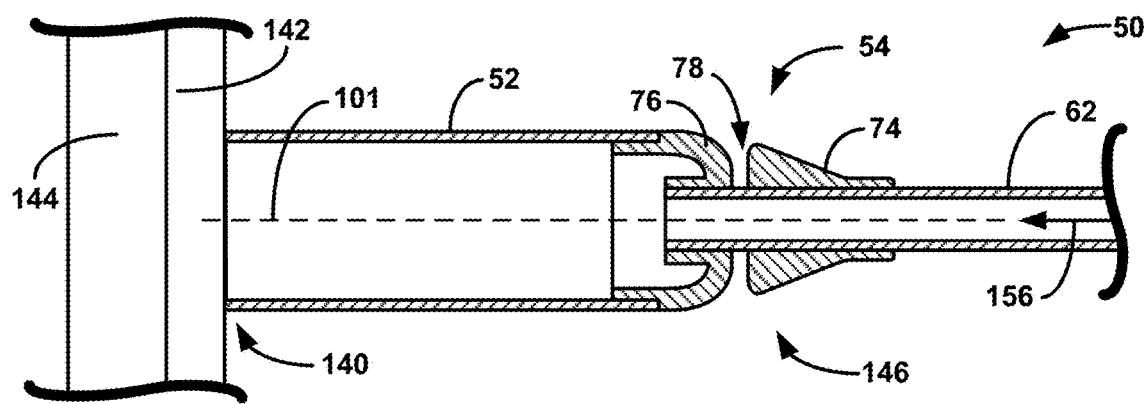
Figure 4C:
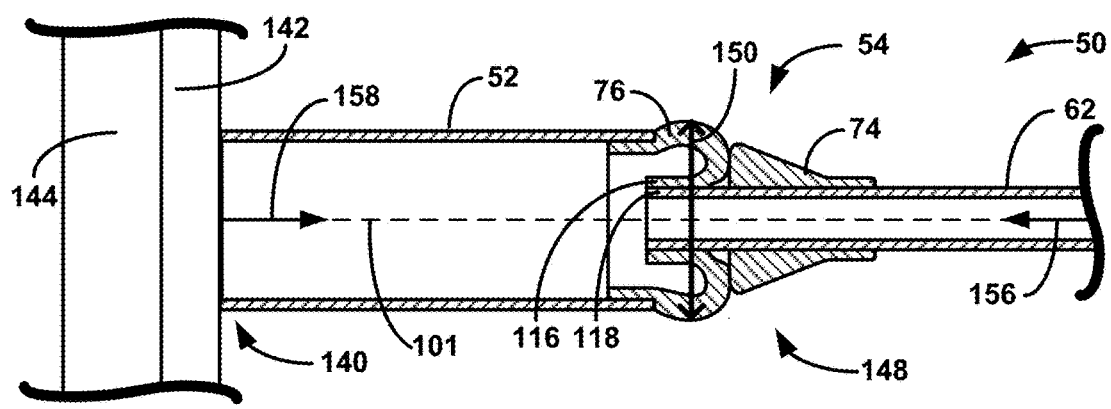

As noted above, compression mechanism 54 may be configured to longitudinally deform in response to an axial force, e.g., greater than a threshold force, that is applied to the delivery device 50 (e.g., an axial force as discussed and depicted in FIGS. 4A-4C). In some examples, compression mechanism 54 may be configured to deform in response to a compressive force, such as a force that is applied to compression mechanism 54 along or parallel a longitudinal axis of delivery device 50 from both a proximal and a distal direction. Compression mechanism 54 may be relatively more deformable than other portions of delivery device 50 in response to the axial force above the threshold force, such that compression mechanism 54 is substantially the only element of delivery device 50 that deforms a significant amount in response to the axial force.

The threshold force may be a force that sufficient to longitudinally compress compression mechanism 54, such that compression mechanism 54 may define the threshold force. Compression mechanism 54 may be configured to define the threshold force as the force applied to compression mechanism when a clinician presses (e.g., using ports of hub 56) deployment bay 52 against tissue at a target site. For example, compression mechanism 54 may define the threshold force as an axial compressive force that is sufficient to compress compression mechanism 54 when deployment bay 52 contacts and presses against right atrium 20 of heart 12 of patient 14 with a force that is insufficient to perforate the tissue of right atrium 20. In some examples, the threshold force may be between 1 or 2 newtons, though in other examples the threshold force may be less or more and/or may include a broader range. In some examples, the threshold force may be higher than a force that is expected to be applied to the compression mechanism 54 during insertion of delivery device 50 into patient 14. Similarly, the threshold force may higher than a force that is expected to be applied to the compression mechanism 54 while delivery device 50 is handled prior to insertion or while deployment bay 52 navigates to a target site of patient 14. In this way, during the course of normal (e.g., expected or planned) actions during a medical device deployment procedure using delivery device 50, compression mechanism 54 may be configured to deform substantially only in response to deployment bay 52 pressing against tissue of target site in order to deploy the medical device.

Compression mechanism 54 may be configured to deform in a predetermined manner. In some examples, compression mechanism 54 may be configured to deform a predetermined amount in response to a force greater than or equal to the threshold force. For example, compression mechanism 54 may be configured to deform by longitudinally compressing, such that axial length 72 of compression mechanism 54 as measured along a longitudinal axis of delivery device 50 is relatively shorter as a result of the deformation. As such, compression mechanism 54 may be configured such that axial length 72 of compression mechanism 54 compresses a predetermined amount to a predetermined shorter length in response to the applied force that is at least the threshold force. Compression mechanism 54 may be configured to be relatively pliable, such that compression mechanism 54 may repeatedly deform and flex back into an uncompressed state in response to the application of and release from a force of at least the threshold force.

Compression mechanism 54 may have a relatively strong shape memory relating to a shape of compression mechanism 54 in the uncompressed state, such that compression mechanism 54 may return to an uncompressed state in response to a lack of forces applied to delivery device 50 that are at least the threshold force. Put differently, compression mechanism 54 may be configured to flex from an uncompressed shape to a predetermined shape once a force applied to compression mechanism 54 exceeds a threshold force, and subsequently deform from the predetermined shape back to the uncompressed shape once the force is no longer applied to compression mechanism 54 or otherwise is reduced to an amount below the threshold force.

Compression mechanism 54 may include proximal component 74 and distal component 76, where proximal component 74 is secured to delivery device 50 at a location that is relatively proximal compared to distal component 76. In certain examples, as depicted in FIG. 2A, both proximal component 74 and distal component 76 may be secured to (e.g., chemically bonded to) elongated member 62. In some examples, proximal component 74 and distal component 76 may define axial gap 78 between them when compression mechanism 54 is in the uncompressed state. Gap 78 may be an axial physical space into which neither proximal component 74 nor distal component 76 longitudinally extend when compression mechanism 54 is in the uncompressed state. An axial length of gap 78 when in this uncompressed state may be substantially equal to the amount of axial compression that compression mechanism 54 may undergo as a result of the force over the threshold force. In some examples the only component of delivery device 50 that longitudinally extends between proximal component 74 and distal component 76 is elongated member 62.

Compression mechanism 54 may deform by "closing" or otherwise shrinking or gap 78, such that at least a portion of proximal component 74 may be configured to longitudinally move closer to at least a portion of distal component 76. In this way, one or both of proximal component 74 and distal component 76 may be configured to longitudinally move in response to a force to define gap 78 to be relatively smaller, or such that gap 78 is no longer present. For example, as compression mechanism 54 deforms, at least a portion of proximal component 74 may contact at least a portion of distal component 76.

In some examples, one of proximal component 74 or distal component 76 may deform relatively more in response to the force above the threshold force. Distal component 76 and proximal component 74 may be made of different materials or define different structures or the like, such that one of the two is relatively more axially stable than the respective other. In some examples, proximal component 74 may be made of a relatively stiffer material than distal component 76, such that distal component 76 deforms relatively more in response to the force above the threshold force than proximal component 74.

In some examples, compression mechanism 54 may include radiopaque elements 90A, 90B (collectively "radiopaque elements 90") that may indicate a deformation of compression mechanism 54. For example, compression mechanism 54 may include radiopaque elements 90 that enable a clinician monitoring an intravenous navigation of delivery device 50 to determine whether and how much compression mechanism 54 has deformed. For example, as depicted in FIG. 2A, compression mechanism 54 may include first radiopaque element 90A on or in proximal component 74 and second radiopaque element 90B on or in distal component 76 and, such that a clinician may track proximal component 74 moving relative to distal component 76, e.g., moving relatively closer to distal component 76 by tracking radiopaque elements 90 moving closer together using various fluoroscopy techniques. In other examples, radiopaque elements 90 may alternatively or additionally be located on delivery device at a location proximal and or distal to compression mechanism 54 (e.g., rather than secured directly to compression mechanism 54). For example, radiopaque element 90A may be secured to elongated member 62 at a location immediately proximal to compression mechanism 54, and/or radiopaque element 90B may be secured to deployment bay 52 at a location immediately distal to compression mechanism 54. Radiopaque elements 90 may be a band of radiopaque materials that is embedded within delivery device 50, a band that runs along an outer circumference of a portion of delivery device 50, a doped portion of delivery device 50 (e.g., relative to adjacent portions), or the like. In other examples, delivery device 50 may alternatively or additionally include echogenic materials rather than or in addition to radiopaque elements 90. For example, delivery device 50 may include two echogenic elements (e.g., carbides) located near where radiopaque elements 90 are located. Echogenic elements may be used to monitor the compression of compression mechanism 54 in response to a force of at least the threshold force using an echocardiogram.

Figure 5A:
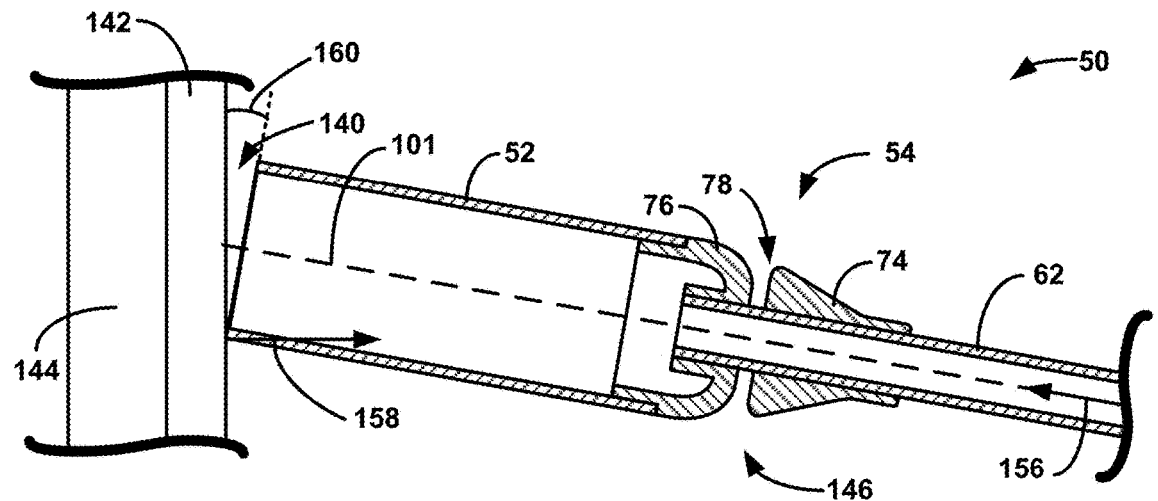
FIGS. 5A and 5B are conceptual and schematic diagrams illustrating cross-sectional views of the delivery device of FIG. 2A as viewed along one of the cut-planes of FIG. 2A as the delivery device approaches and presses against, respectively, a target site in a patient from an angle.
Figure 5B:
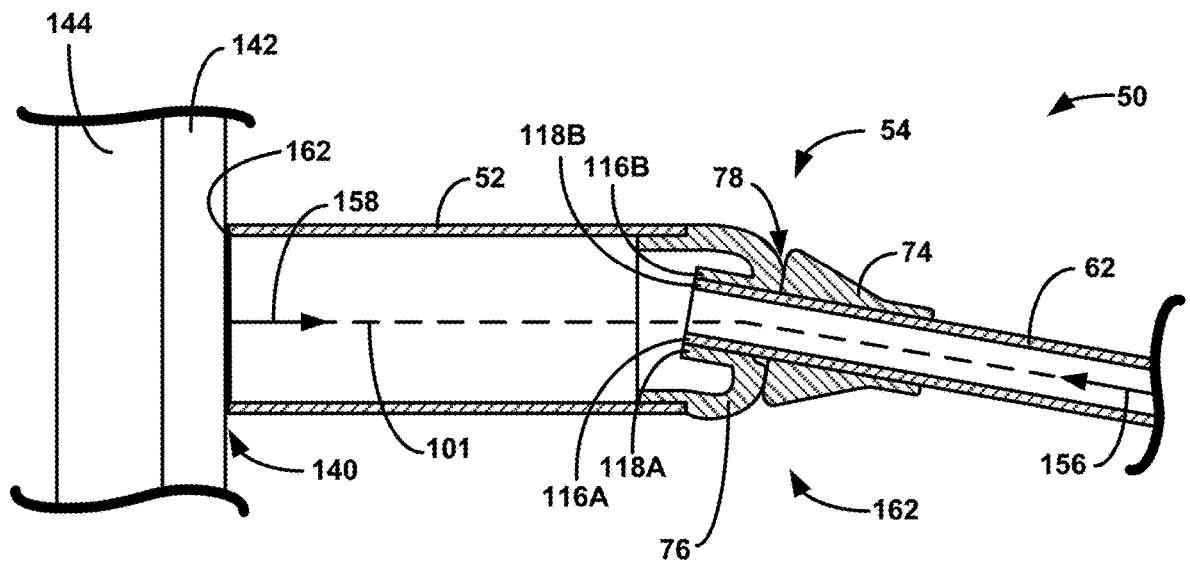

In some examples, as depicted in FIG. 2A, compression mechanism 54 may be at a location immediately proximal to deployment bay 52. In other examples (not depicted), compression mechanism 54 may be located along a length of deployment bay 52 or along a length of elongated member 62. Locating compression mechanism 54 immediately proximal to deployment bay 52 may enable delivery device 50 to deform non-symmetrically about the longitudinal axis, e.g., more on one side of a longitudinal axis than another side, to enable deployment bay 52 to contact a target site flush (e.g., as depicted in FIGS. 5A and 5B). Further, locating compression mechanism 54 immediately proximal to deployment bay 52 may enable delivery device 50 to be removed from patient 14 through an introducer sheath with relatively less force as a result of proximal component 74 sloping from a radius that is relatively close to a radius of elongated member 62 to a radius that is relatively close to a radius of deployment bay 52.

Figure 3:
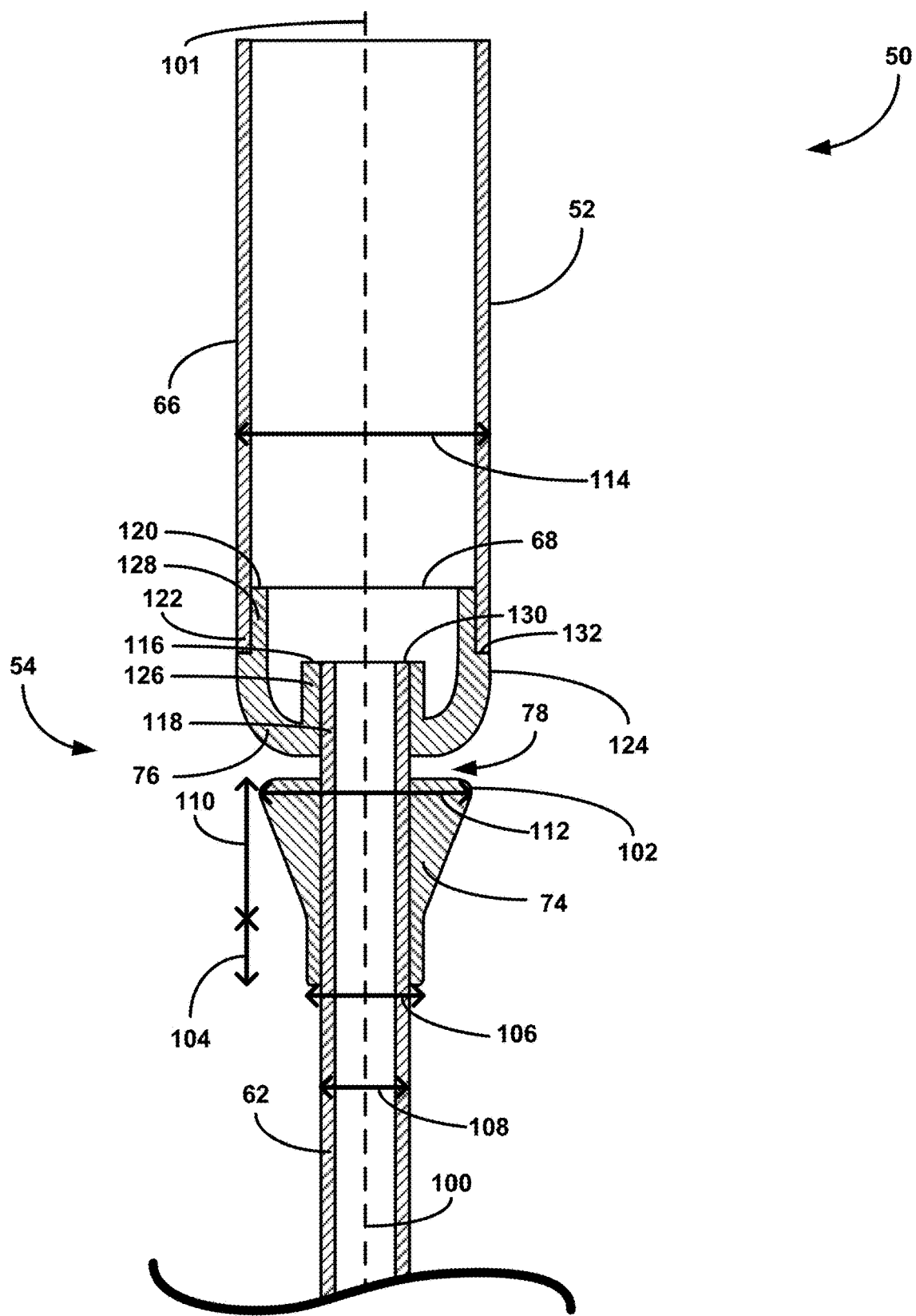
FIG. 3 is a conceptual and schematic diagram illustrating a cross-sectional view of the deployment bay and compression mechanism of the delivery device of FIG. 2A as viewed along another of the cut-planes of FIG. 2A.

FIG. 3 depicts a conceptual and schematic diagram of a cross-sectional view of deployment bay 52 and compression mechanism 54 as taken along cross-sectional cut plane 51 of FIG. 2A. FIG. 3 depicts delivery device 50 before force greater than a threshold force has been applied to compression mechanism 54, such that compression mechanism 54 is in an uncompressed state in FIG. 3. Within this uncompressed state, gap 78 is at a relatively fully maximized length as defined between proximal component 74 and distal component 76. As depicted in FIG. 3, elongated member 62 includes lumen 100. Lumen 100 may serve any of the purposes described herein, such as a medical device lumen (e.g., primary lumen 80 of FIGS. 2B and 2C) to transport or house the insertable or implantable medical device during intravenous navigation, a guidewire lumen for a guidewire, a deployment lumen to house a deployment mechanism, or the like. In some examples, deployment bay 52, compression mechanism 54, and elongated member 62 may each be substantially symmetrical as reflected around longitudinal axis 101 of delivery device 50, such that the depicted cross-sectional view of FIG. 3 is substantially similar to all views of deployment bay 52, compression mechanism 54, and elongated member 62 as taken along a plane that is parallel with and intersects longitudinal axis 101.

As depicted in FIG. 3, proximal component 74 may be a relatively solid component, such that proximal component 74 may define few or substantially no lumens or recesses between outer surface 102 of proximal component 74 and elongated member 62. Outer surface 102 of proximal component 74 may be substantially continuous. Further, proximal component 74 may be made from a relatively stiff material, e.g., when compared to distal component 76, such as a stiff version of PEBA such as Pebax® 70D or Pebax® 72D. As a result of proximal component 74 being relatively solid and/or proximal component 74 including a relatively stiff material, proximal component 74 may be relatively less likely to deform, e.g., when compared to distal component 76, in response to the force above the threshold force being applied to compression mechanism 54.

As depicted in FIG. 3, a radius of proximal component 74 may increase as proximal component 74 extends distally. For example, a proximal-most length 104 of proximal component 74 may define first outer diameter 106 that is only slightly greater (e.g., 10-20% greater) than diameter 108 of elongated member 62, while distal-most length 110 of elongated member 62 may slope or angle from first outer diameter 106 out to second outer diameter 112 that is substantially greater (e.g., 50-150% greater) than outer diameter 108 of elongated member 62. In some examples, the second diameter 112 may be relatively similar to diameter 114 of distal component 76 and/or deployment bay 52. Configuring proximal component 74 of compression mechanism 54 to extend radially out from diameter 106 that is similar to diameter 108 of elongated member 62 to diameter 112 that is similar to diameter 114 of deployment bay 52 may reduce a necessary force to retract deployment bay 52 from an introducer sheath after a medical device is successfully deployed as described herein. Further, configuring proximal component 74 of compression mechanism 54 to define an increasing radius as proximal component extends distally may reduce a possibility of elongated member 62 kinking during use or navigation of delivery device 50.

In some examples, proximal component 74 may define a substantially constant angle or slope of outer surface 102 between first outer diameter 106 and second outer diameter 112. In other examples, proximal component 74 may "step" between a plurality of increasing diameters along second length 110 to transition between first diameter 106 and second diameter 112 (e.g., rather than angling or sloping between the two diameters).

Conversely, as depicted in FIG. 3, distal component 76 may define a flexible sheet that is flexed within compression mechanism 54. The flexible sheet of the distal component 76 may define first end 116 and second end 120. A proximal portion 126 of the sheet that is adjacent first end 116 may be attached (e.g., mechanically or chemically secured) to distal portion 118 of elongated member 62 such that first end 116 is longitudinally aligned with distal end 130 of elongated member 62. Further, distal portion 128 of the sheet that is adjacent second end 120 may be attached to proximal portion 122 of deployment bay 52 such that distal portion 128 extends distal to proximal end 132 of deployment bay 52 (e.g., and second end 120 of sheet is somewhat distal to proximal end 132. Put differently, a first end of a flexible sheet of distal component 76 may be secured to elongated member 62 and a second end may be secured to deployment bay 52 such that lengths of the flexible sheet that are adjacent respective ends of the flexible sheet are secured to the elongated member 62 in a direction proximal to both ends. Both proximal portion 126 and distal portion 128 of sheet of distal component may be secured to elongated member 62 and deployment bay 52, respectively, most or substantially all of the way around the perimeter of distal component 76.

Similar to proximal component 74, distal component 76 may define a substantially continuous outer surface 124 (e.g., a surface that defines the greatest radius of distal component 76 along any one plane that is perpendicular to longitudinal axis 101), such that outer surface 124 substantially avoids defining ridges or holes. Distal component 76 may be made of relatively soft and/or flexible materials, e.g., when compared to proximal component 74, such as Pebax® between 25D and 40D, overmolded or melted thermoplastic elastomers (TPEs), or other elastomers applied using bonding agents or mechanical attachment elements. As a result of distal component 76 defining a sheet that is attached at first end 116 to elongated member 62 and attached at second end 120 to deployment bay 52 and/or distal component 76 being made of a relatively softer and/or more flexible material, distal component 76 may be configured to deform (e.g., axially compress) when exposed to the force above the threshold force.

FIGS. 4A-4C are conceptual and schematic diagrams illustrating cross-sectional views as taken from cut-plane 51 of FIG. 2A of delivery device 50 navigating to and interfacing with target site 140 in patient 14. As described herein, target site 140 may be in right atrium 20 of heart 12 of patient 14, though delivery device 50 may be used to delivery an insertable or implantable medical device to other areas of patient 14 in other examples. Target site 140 may include layer of tissue 142 to which insertable or implantable medical device is configured to pierce during deployment in order to secure the medical device to the target site 140. Put differently, in some examples insertable or implantable medical device is configured to mechanically attach itself to tissue layer 142 of target site. The medical device may be configured to secure itself to tissue layer 142 using distal tines, or some other fixation element(s) that are configured to distally extend from deployment bay 52 when medical device is deployed (e.g., using deployment mechanism 88 of FIGS. 2B-2D that distally pushes medical device out of distal opening 70 of deployment bay). Further, in some examples, target site 140 may include muscle tissue 144 that is beneath tissue 142 from the reference of delivery device 50, i.e., further away from delivery device than tissue 142.

As depicted in FIG. 4A, a clinician has navigated delivery bay 52 of delivery device 50 to target site 140, such that a medical device (not depicted in FIG. 4A for purposes of clarity) housed at least partially within deployment bay 52 is adjacent target site 140. As depicted, before contacting target site 140, compression mechanism 54 may be in uncompressed state 146, where uncompressed state 146 is substantially similar to the configuration of proximal component 74 and distal component 76 described herein.

Deployment bay 52 may be navigated proximal to target site 140 as a result of a distal force 156 applied to delivery device 50. A clinician may apply distal force 156 by, e.g., manually applying a force to one or more proximal components of delivery device 50. For example, a clinician may apply distal force 156 to hub 56 (depicted in FIG. 2A), or otherwise apply distal force 156 using hub 56. Distal force 156 may be less than the threshold force that is configured to deform compression mechanism 54.

FIG. 4B depicts the deployment bay 52 contacting tissue 142 at target site 140. Deployment bay 52 may contact tissue at target site 140 as a result of distal force 156 (e.g., as applied by clinician). As is depicted in FIG. 4B, compression mechanism 54 may define gap 78 between proximal component 74 and distal component 76 when delivery device 50 first contacts target site 140.

FIG. 4C depicts delivery device 50 as delivery device 50 is pressed into target site 140 such that compression mechanism 54 deforms into compressed state 148. Compression mechanism 54 may deform into compressed state 148 as a result of normal force 158 from target site 140. Target site 140 may apply normal force 158 to compression mechanism 54 (e.g., as through deployment bay 52) as a result of clinician maintaining distal force 156 on delivery device 50 as deployment bay 52 contacts target site 140. Normal force 158 and distal force 156, in conjunction, may meet or surpass the threshold force, such that compression mechanism 54 deforms into compressed state 148.

As depicted, when in compressed state 148, compression mechanism 54 may substantially cease defining gap 78. Compression mechanism 54 may substantially cease defining gap 78 as a result of distal component 76 deforming. As depicted in FIG. 4C, deforming may include distal component 76 bowing outward such that distal component 76 defines flexed diameter 156 that is greater than previous diameter 114 of distal component 76. When deformed into compressed state 148, the deformation of compression mechanism 54 may be substantially mirrored, i.e., substantially symmetric, around longitudinal axis 101. Compression mechanism 54 may deform into the substantially mirrored compressed state 148 as a result of both distal force 156 and normal force 158 being substantially aligned with (e.g., substantially coaxial with) longitudinal axis 101. Further, elongated member 62 may be configured to not compress or deform in response to the combined distal force 156 and normal force 158. For example, elongated member 62 may be made of a material that will substantially avoid compressing in response to forces that are similar to the distal force 156 and normal force 158.

As a result of elongated member 62 not compressing from the combined distal force 156 and normal force 158, distal portion 118 of elongated member 62 may extend distally toward deployment bay 52 once compression mechanism 54 deforms. In some examples, distal portion 118 of elongated member 62 may extend distally an amount sufficient to deploy a medical device housed within deployment bay 52. For example, distal portion 118 may extend distally relative to deployment bay 52 and contact and distally pushing a proximal end of the housed medical device. The distal portion 118 may therein push the medical device an amount sufficient to "activate" or otherwise cause the fixation elements to secure the medical device against target site 140.

As a result of distal portion 118 of elongated member 62 being attached to first end 116 of distal component 76, first end 116 may also extend distally toward deployment bay 52 in response to compression mechanism 54 deforming. As a result of the radiopaque elements 90 (as depicted in FIG. 2A) of compression mechanism 54, the deformation of compression mechanism 54 may provide visual feedback to clinician (e.g., when using fluoroscopy techniques) once clinician successfully applies distal force 156 and navigates deployment bay 52 to target site 140 such that the respective insertable or implantable medical device is ready to be deployed. Providing feedback to a clinician may improve an ability of a clinician to verify that an insertable or implantable medical device has been navigated to a proper spot and is a proper axial distance and orientation from a wall of target site 140, reducing or eliminating a possibility of suboptimal deployments as a result of premature deployment.

FIGS. 5A and 5B depict conceptual and schematic cross-sectional diagrams as taken along cut plane 51 from FIG. 2A of delivery device 50 navigating to and interfacing with target site 156 at angle 160 relative to longitudinal axis 101 of delivery device 50. Put differently, FIG. 5A depicts a surface of distal end 164 of deployment bay 52 defining an angle 160 with a surface of target site 140 (e.g., rather than the two surfaces being flush or parallel with each other). Depending upon particular geometries of venous systems of patients 14, in some examples target site 140 may be approached at such angles 160. For example, as depicted in FIG. 5A, as a result of approaching target site 140 at angle 160, only one side 162 of distal end 164 of deployment bay 52 may initially contact target site 140. If deployment bay 52 deployed insertable or implantable medical device when distal end 164 of deployment bay 52 is at angle 160 to target site 140, tines or fixation elements of insertable or implantable medical device may have difficulty fixating to target site 140 as intended. For example, tines or fixation elements of insertable or implantable medical device that are close to side 162 contacting target site 140 may secure to muscle tissue 144, while tines or fixation elements opposite side 162 may not successfully secure to any layer of target site 140.

FIG. 5B depicts compression mechanism 54 once compression mechanism 54 compresses as a result of contacting target site 140 at angle 160. As depicted in FIG. 5B, compression mechanism 54 deforms into unbalanced or asymmetrical compressed state 162. In unbalanced compressed state 162, compression mechanism 54 may deform more on one side than on an opposing side (e.g., sides as viewed across longitudinal axis 101). For example, in unbalanced compressed state 162, compression mechanism may define different shapes on different sides of longitudinal axis 101, such that one side of first end 116A (and therein the respective side of distal portion 118A) is relatively distal to second side of first end 116B (and respective side of distal portion 118B).

Compression mechanism 54 may compress into unbalanced compressed state 162 as a result of normal force 158 being at angle 160 to longitudinal axis 101 when deployment bay 52 contacts target site 140 (e.g., as depicted in FIG. 5A). Compression mechanism 54 deforming into unbalanced compressed state 162 may substantially align (e.g., make colinear) longitudinal axis 101 of delivery device 50 and normal force 158. Put differently, compression mechanism 54 may deform such that distal end 164 of deployment bay 52 is flush with target site 140. By deforming such that distal end 164 of deployment bay 52 is flush with target site 140, delivery system may improve an ability of delivery device 50 deploying an insertable or implantable medical device such that fixation elements are secured to layer of tissue 142 without penetrating muscle tissue 144.

Figure 6A:
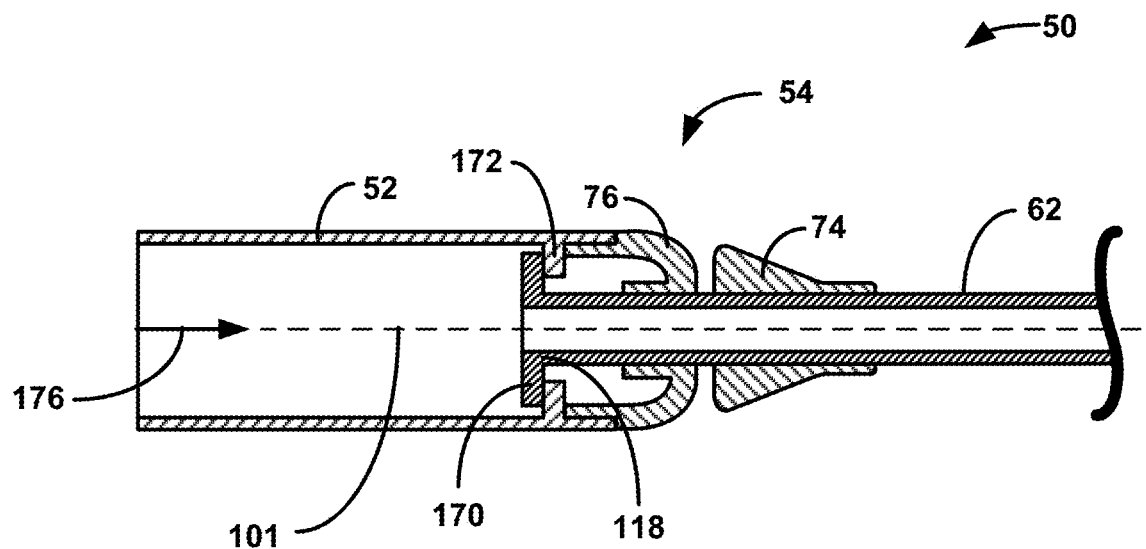
FIG. 6A is a conceptual and schematic diagram illustrating a cross-sectional view of the delivery device of FIG. 2A as viewed along one of the cut-planes of FIG. 2A with a distal stop attached to the elongated member.

In some examples, delivery device 50 may include features that are configured to improve an ability of deployment bay 52 and compression mechanism 54 to be retracted out of an introducer sheath. For example, FIG. 6A depicts a conceptual and schematic diagram illustrating a cross-sectional view of delivery device 50 of FIG. 2A as viewed along cut-plane 51 of FIG. 2A with distal stop 170 attached to distal end 118 of elongated member 62. Distal stop 170 may extend radially out from distal end 118 of elongated member 62 to interface with ridge 172 of deployment bay 52 as delivery device 50 is withdrawn. Ridge 172 may extend radially in from an inner surface of deployment bay 52. As a clinician applies withdrawal force 176 to delivery device 50 (e.g., by pulling upon hub 56 or elongated member 62 that is external to patient 14) distal stop 170 may press against ridge 172. Distal stop 170 may improve an ability of compression mechanism 54 to maintain a stable structure as delivery device 50 is withdrawn through an introducer sheath by reducing an amount that distal component 76 may flex.

Figure 6B:
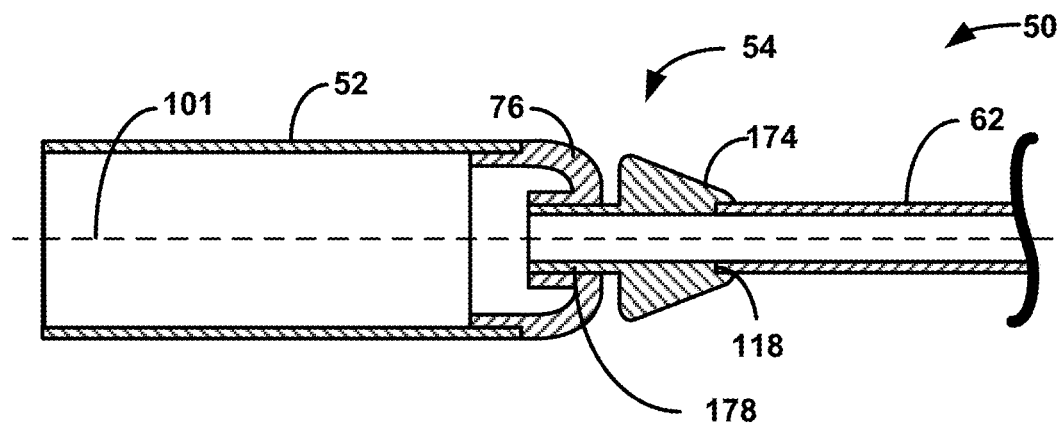
FIG. 6B is a conceptual and schematic diagram illustrating a cross-sectional view of the delivery device of FIG. 2A as viewed along one of the cut-planes of FIG. 2A with a different proximal component.

In some examples, elongated member 62 may terminate at a proximal end of compression mechanism 54. For example, FIG. 6B depicts a conceptual and schematic diagram illustrating a cross-sectional view of delivery device 50 of FIG. 2A as viewed along cut plane 51 with elongated member 62 that does not extend past a proximal end of compression mechanism 54. Compression mechanism 54 includes proximal component 174 that may be substantially similar to proximal component 74 of FIGS. 2A-5B with the exception of any differences described herein. Proximal component 174 may include tube 178 that extends axially from proximal component 174. Tube 178 may have a substantially similar outer diameter and inner lumen as elongated member 62. Tube 178 may extend from proximal component 174 aligned with longitudinal axis 101 of delivery device 50. Tube 178 may be fixedly attached to distal component 76. Tube 178 may be fixedly attached to distal component 76 in a substantially similar manner as how elongated member 62 was fixedly attached to distal component 76. In some examples, configuring compression mechanism 54 such that only proximal component 174 is directly secured to elongated member 62 (e.g., such that proximal component 174 is then secured to distal component 76) may functionally "stiffen" compression mechanism 54 therein increasing a threshold force that may compress compression mechanism 54.

As discussed herein, in some examples a compression mechanism may be located along a length of a deployment bay. In such examples, the compression mechanism may define a relatively "weaker" element, e.g., less stiff or resilient in one or more directions or along one or more axes, such as a direction along the longitudinal axis of the delivery device, compared to longitudinally adjacent portions of the deployment bay. As a result of a such weaker elements, the length of the deployment bay itself may compress in response to the force above the threshold force. The weaker element may include a relatively softer material, a relatively thinner wall, or a structure that is relatively less braced against longitudinal compression in comparison to the longitudinally adjacent portions of the deployment bay.

Radiopaque elements or other elements visible via imaging may be placed on both longitudinal sides of the compressions mechanism, such that a compression of the deployment bay as a result of the weaker element compressing may be monitored. Examples of compression mechanisms that include "weaker" elements relative to longitudinally adjacent portions of a deployment bay may be found in FIGS. 7A-14B.

FIGS. 7A and 7B are conceptual and schematic diagrams of side views of an example medical delivery device 250 in uncompressed state 246 and compressed state 248. Delivery device 250 may be substantially similar to delivery device 50 except for any differences described herein. Delivery device 250 may define longitudinal axis 201 and may include deployment bay 252. Deployment bay 252 may be substantially similar to deployment bay 52 except for any differences described herein.

Delivery device 250 includes compression mechanism 254, which may be configured to axially compress as described herein to provide similar utility as described above with regards to compression mechanism 54. As depicted in FIGS. 7A and 7B, delivery device 250 may include compression mechanism 254 within a length of deployment bay 252 (e.g., such that deployment bay 252 is on either axial side of compression mechanism 254). In other examples (not depicted), compression mechanism 254 may be at other locations along delivery device 250, such as immediately proximal to deployment bay 252 (e.g., similar to a depicted placement of compression mechanism 54 in delivery device 50 in FIGS. 2A-6B), or at other locations along an elongated member of delivery device 250 (e.g., an elongated member similar to elongated member 62). In some examples, compression mechanism 254 may be at a distal end of delivery device 250 such that compression mechanism 254 is functionally the distal tip of delivery device 250 (not depicted). In such examples where compression mechanism 254 is at a distal tip, compression mechanism 254 may deform such as by flaring radially outward to indicate the prescribed force while also being configured to assure a normal angle for optimal deployment as described herein.

Compression mechanism 254 may be made out of a different material than deployment bay 252. For example, compression mechanism 254 may be made out of a relatively more axially compressible and/or otherwise deformable material than deployment bay 252. In some examples, other than being constructed of a different material, compression mechanism 254 may be structurally similar to deployment bay 252. For example, deployment bay 252 may define a substantially cylindrical shape that is centered on longitudinal axis 201, such that deployment bay 252 may define a substantially circular cross-section as viewed along a cut plane that is perpendicular to longitudinal axis 201. In this example, compression mechanism 254 may define substantially the same cylindrical shape with a substantially similar circular cross-sectional shape when compression mechanism 254 is in uncompressed state 246. Put differently, deployment bay 252 may define a substantially constant internal radius 260 and wall thickness 262 along its length, and compression mechanism 254 may define substantially constant internal radius 264 and wall thickness 266 that is substantially similar to internal radius 260 and wall thickness 262 of deployment bay 252.

Deployment bay 252 may be navigated to a target site (e.g., similar to target site 140 of FIGS. 4A-5B) by distal force 256 which may be substantially similar to distal force 156. Once deployment bay 252 contacts a tissue layer of patient 14 at the target site, the tissue layer may apply normal force 258 to deployment bay 252 (and therein compression mechanism 254) as a result of ongoing distal force 256. Compression mechanism 254 may deform from uncompressed state 246 to compressed state 248 of FIG. 7B. In some examples, compressed state 248 of compression mechanism 254 may be predetermined. For example, a "crumpled" shape of compression mechanism 254 as depicted in FIG. 7B may be predetermined with compression mechanism 254 extending radially out to first radius 268 that is larger than inner radius 264 of uncompressed state 264 and also extending radially in to second radius 270 that is smaller than inner radius 264, such that compression mechanism 254 may reliably and/or predictably deform to the shape of crumpled state 248. Further, in some examples, compression mechanism 254 may be configured to repeatedly deform in response to distal force 256 and normal force 258 to compressed state 248 and thereinafter return to uncompressed state 246 once normal force 258 and/or distal force 256 is reduced or lifted (e.g., unapplied).

In some examples (not depicted), delivery device 250 may include one or more radiopaque elements configured to indicate an amount that compression mechanism 254 longitudinally compresses in response to a force above the threshold force. For example, similar to radiopaque markers elements 90 as depicted in FIG. 2A, delivery device 250 may include a first radiopaque element located adjacent a proximal portion of compression mechanism 254 and include a second radiopaque element adjacent a distal portion of compression mechanism 254. Using two such radiopaque elements, a clinician may track a compression of compression mechanism 254 from uncompressed state 246 to compressed state 248.

Figure 8B:
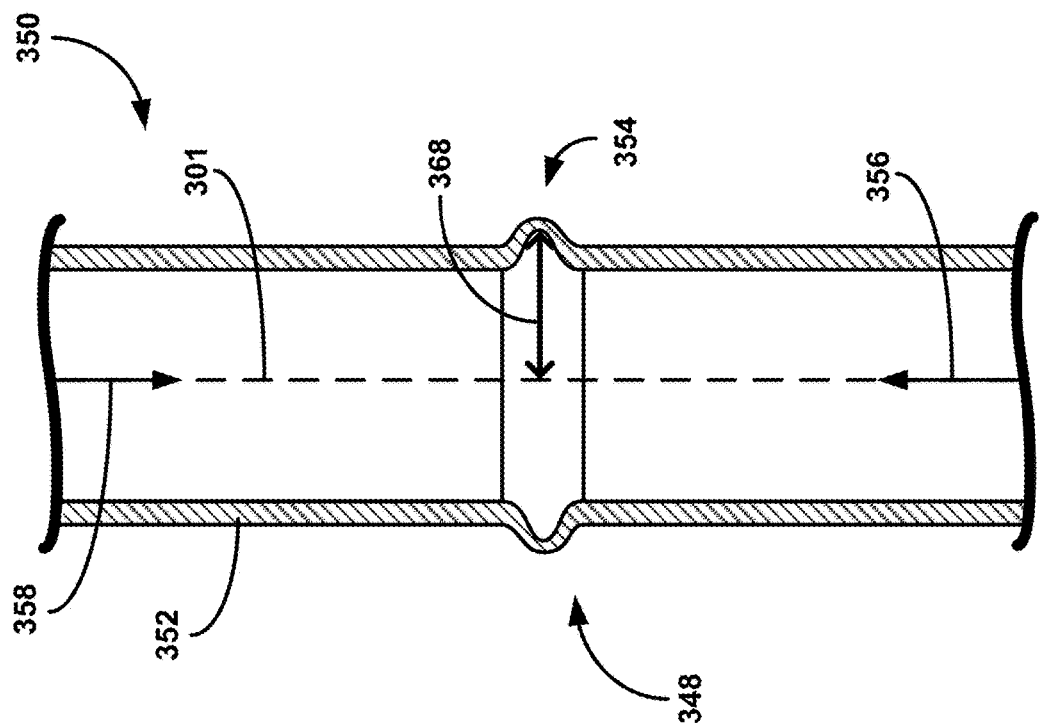
FIGS. 8A and 8B are conceptual and schematic diagrams illustrating cross-sectional views of an uncompressed and compressed state, respectively, of an example delivery device that includes an example compression mechanism that defines a first circumferential cut-out.
Figure 8A:
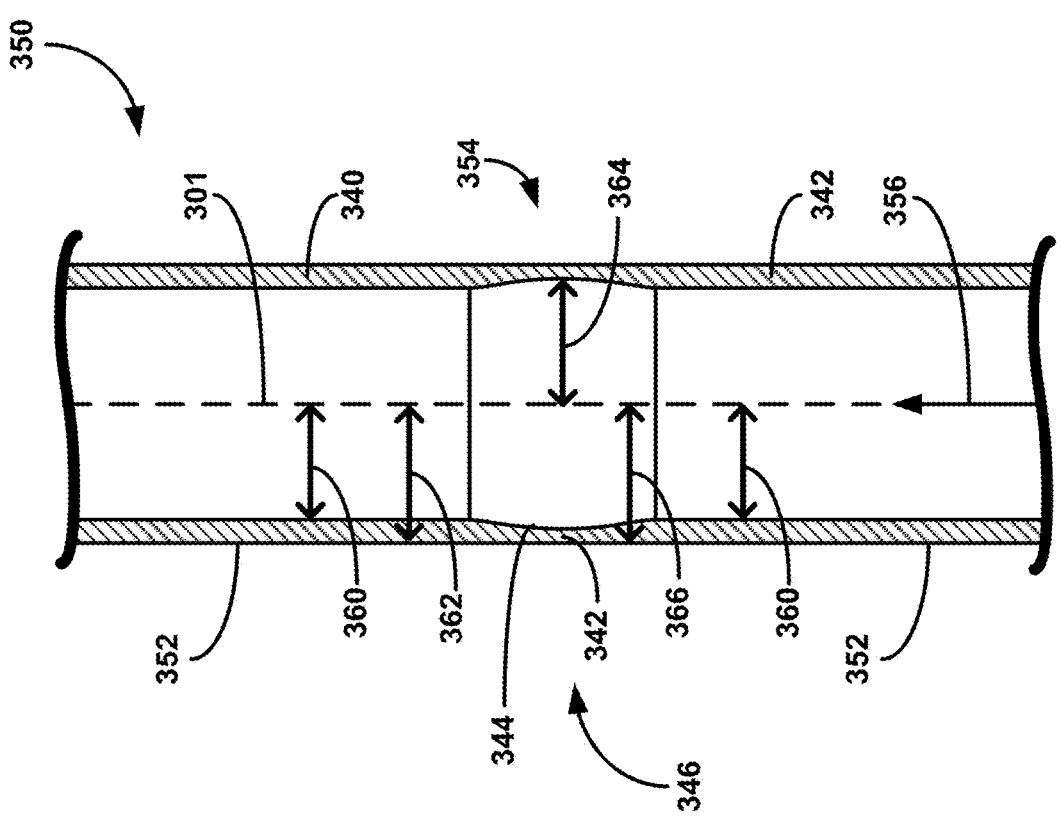

FIGS. 8A and 8B are conceptual and schematic diagrams of side views of an example medical delivery device 350 in uncompressed state 346 and compressed state 348. Delivery device 350 may be substantially similar to delivery device 50 and delivery device 250 except for any differences described herein. Delivery device 350 may define longitudinal axis 301 and may include deployment bay 352. Deployment bay 352 may be substantially similar to deployment bay 52 except for any differences described herein.

Delivery device 350 includes compression mechanism 354, which may be configured to axially compress as described herein to provide similar utility as described above with regards to compression mechanism 54 and compression mechanism 254. As depicted in FIGS. 8A and 8B, delivery device 350 may include compression mechanism 354 within a length of deployment bay 352 (e.g., such that deployment bay 352 is on either axial side of compression mechanism 354). In other examples (not depicted), compression mechanism 354 may be at other locations along delivery device 350, such as immediately proximal to deployment bay 352 (e.g., similar to a depicted placement of compression mechanism 54 as on delivery device 50 in FIGS. 2A-6B), or at other locations along an elongated member of delivery device 350 (e.g., an elongated member similar to elongated member 62). In some examples, compression mechanism 354 may be at a distal end of delivery device 350 such that compression mechanism 354 is functionally the distal tip of delivery device 350 (not depicted). In such examples where compression mechanism 354 is at a distal tip, compression mechanism 354 may deform such as by flaring radially outward to indicate the prescribed force while also being configured to assure a normal angle for optimal deployment as described herein.

At least a portion of compression mechanism 354 may define walls that gradually thin (e.g., define less radial width across a single wall) along an axial length of compression mechanism 354 relative to walls of deployment bay 352. For example, along a length of deployment bay 352, deployment bay 352 may include tubular wall 340 that defines a substantially cylindrical shape and is centered on longitudinal axis 301. Tubular wall 340 may define a substantially constant inner radius 360 (as measured from longitudinal axis 301) and a substantially constant outer radius 362 along the length of deployment bay 352. Similarly, compression mechanism 354 may define tubular wall 342 that is substantially aligned with longitudinal axis 301. In some examples, inner surface 344 of compression mechanism 354 may extend radially out from longitudinal axis 301 to define internal radius 364 that is relatively larger than internal radius 360 of deployment bay 352. Inner surface 344 of compression mechanism 354 may slope or angle from inner radius 360 of deployment bay 352 to relatively greater inner radius 364 of compression mechanism 354 on both axial ends of compression mechanism 354, such that inner surface 344 defines a smooth transition from inner radius 360 to inner radius 364 and then back to inner radius 360.

In some examples, tubular wall 342 of compression mechanism 354 may define outer radius 366 to be substantially similar to outer radius 362 of deployment bay 352, though in other examples an outer surface of compression mechanism 354 may extend radially in toward longitudinal axis 301 to define outer radius 366 that is substantially smaller than outer diameter 362 of deployment bay 352. In these examples, compression mechanism 354 may be made of substantially the same materials as deployment bay 352, but may be made of one or more different materials in some examples.

Deployment bay 352 may be navigated to a target site (e.g., similar to target site 140 of FIGS. 4A-5B) by distal force 356 which may be substantially similar to distal force 156 and distal force 256. Once deployment bay 352 contacts a tissue layer of patient 14 at the target site, the tissue layer may apply normal force 358 to deployment bay 352 (and therein compression mechanism 354) as a result of ongoing distal force 356. Compression mechanism 354 may deform from uncompressed state 346 to compressed state 348 of FIG. 8B. In some examples, compressed state 348 of compression mechanism 354 may be predetermined. For example, a "crumpled" shape of compression mechanism 354 as depicted in FIG. 8B may be predetermined with compression mechanism 354 extending radially out to define inner crumpled radius 368 that is larger than inner radius 364 of compression mechanism 354 when in uncompressed state 364. In this way, compression mechanism 354 may reliably and/or predictably deform to the shape of crumpled state 348. Further, in some examples, compression mechanism 354 may be configured to repeatedly deform in response to distal force 356 and normal force 358 to compressed state 348 and thereinafter return to uncompressed state 346 once normal force 358 and/or distal force 356 is reduced or lifted (e.g., unapplied).

In some examples (not depicted), delivery device 350 may include one or more radiopaque elements configured to indicate an amount that compression mechanism 354 longitudinally compresses in response to a force above the threshold force. For example, similar to radiopaque markers elements 90 as depicted in FIG. 2A, delivery device 350 may include a first radiopaque element located adjacent a proximal portion of compression mechanism 354 and include a second radiopaque element adjacent a distal portion of compression mechanism 354. Using two such radiopaque elements, a clinician may track a compression of compression mechanism 354 from uncompressed state 346 to compressed state 348.

Figure 9B:
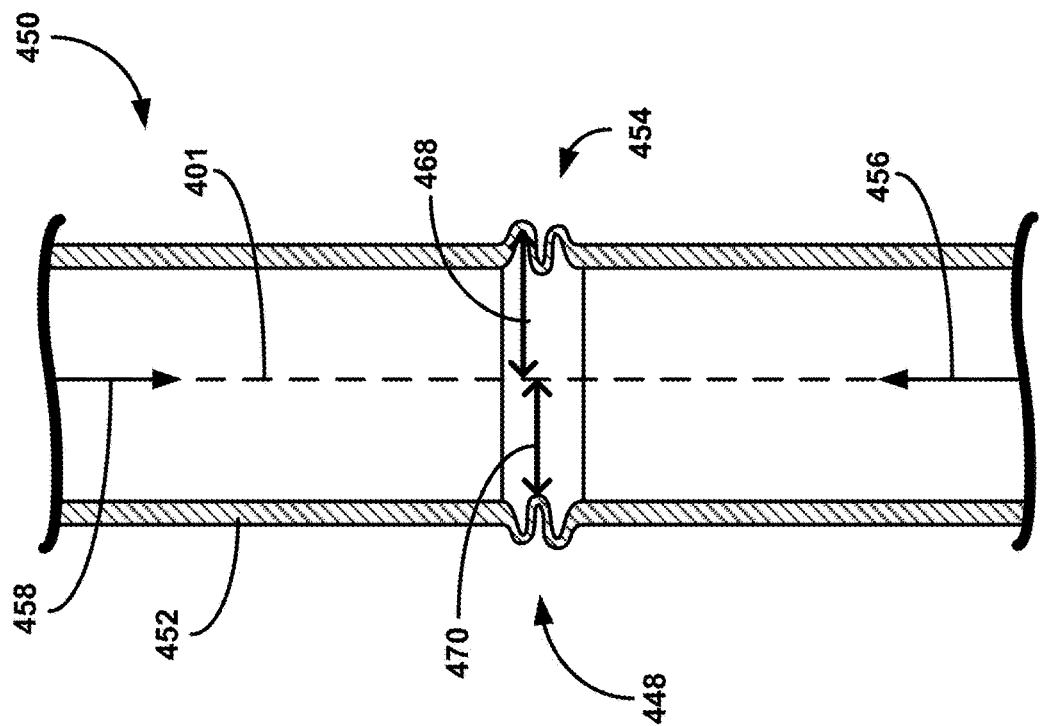
FIGS. 9A and 9B are conceptual and schematic diagrams illustrating cross-sectional views of an uncompressed and compressed state, respectively, of an example delivery device that includes an example compression mechanism that defines a second circumferential cut-out.
Figure 9A:
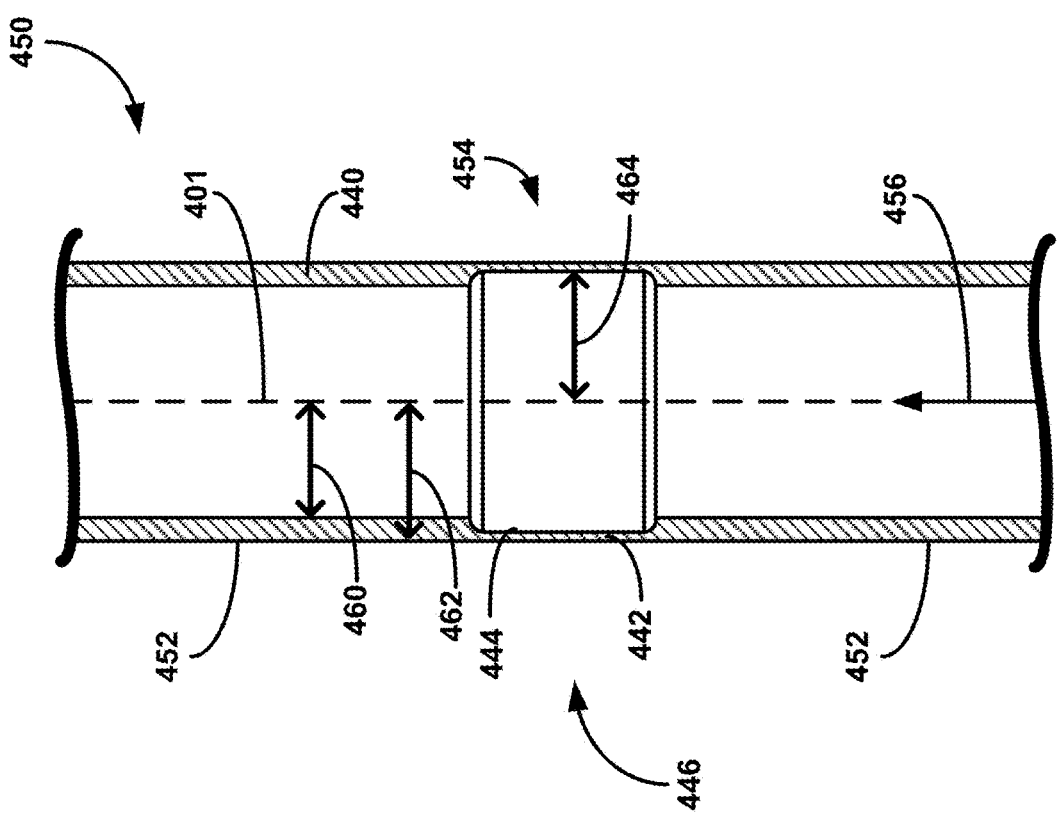

FIGS. 9A and 9B are conceptual and schematic diagrams of side views of an example medical delivery device 450 in uncompressed state 446 and compressed state 448. Delivery device 450 may be substantially similar to delivery device 50, delivery device 250, and delivery device 350 except for any differences described herein. Delivery device 450 may define longitudinal axis 401 and may include deployment bay 452. Deployment bay 452 may be substantially similar to deployment bay 52, deployment bay 252, and/or deployment bay 352 except for any differences described herein.

Delivery device 450 includes compression mechanism 454, which may axially compress as described herein to provide similar utility as described above with regards to compression mechanism 54, compression mechanism 254, and compression mechanism 354. As depicted in FIGS. 9A and 9B, delivery device 450 may include compression mechanism 454 within a length of deployment bay 452 (e.g., such that deployment bay 452 is on either axial side of compression mechanism 454). In other examples (not depicted), compression mechanism 454 may be at other locations along delivery device 450, such as immediately proximal to deployment bay 452 (e.g., similar to a depicted placement of compression mechanism 54 as on delivery device 50 in FIGS. 2A-6B), or at other locations along an elongated member of delivery device 450 (e.g., an elongated member similar to elongated member 62). In some examples, compression mechanism 454 may be at a distal end of delivery device 450 such that compression mechanism 454 is functionally the distal tip of delivery device 450 (not depicted). In such examples where compression mechanism 454 is at a distal tip, compression mechanism 454 may deform such as by flaring radially outward to indicate the prescribed force while also being configured to assure a normal angle for optimal deployment as described herein.

Compression mechanism 454 may define relatively thinner outer walls than deployment bay 452. For example, along a length of deployment bay 452, deployment bay 452 may define tubular wall 440 that defines a substantially cylindrical shape that is centered on longitudinal axis 401. Tubular wall 440 of deployment bay 452 may define a substantially constant internal radius 460 (as measured from longitudinal axis 401) and a substantially constant outer radius 462 along the length of deployment bay 452. Similarly, compression mechanism 454 may define tubular wall 442 that is substantially aligned with longitudinal axis 401 and defines a substantially constant radius 464 along a length of compression mechanism 454. Inner radius 464 of compression mechanism 454 may be greater than inner radius 460, such that tubular wall 442 of compression mechanism 454 may be thinner than tubular wall 440 of deployment bay 452.

In some examples, inner surface 444 of compression mechanism 454 may define a smooth angle or curve from inner radius 460 of deployment bay 452 to inner radius 464 of compression mechanism 454. Inner surface 444 may define such a curve angle or curve on both axial ends of compression mechanism 454. In certain examples, compression mechanism 454 may be made of substantially the same materials as deployment bay 452.

Deployment bay 452 may be navigated to a target site (e.g., similar to target site 140 of FIGS. 4A-5B) by distal force 456 which may be substantially similar to distal force 156, distal force 256, and distal force 356. Once deployment bay 452 contacts a tissue layer of patient 14 at the target site, the tissue layer may apply normal force 458 to deployment bay 452 (and therein compression mechanism 454) as a result of ongoing distal force 456. Compression mechanism 454 may deform from uncompressed state 446 to compressed state 448 of FIG. 9B. In some examples, compressed state 448 of compression mechanism 454 may be predetermined. For example, a "crumpled" shape of compression mechanism 454 as depicted in FIG. 9B may be predetermined with compression mechanism 454 extending radially out to first radius 468 that is larger than inner radius 464 of uncompressed state 464 and also extending radially in to second radius 470 that is smaller than inner radius 464, such that compression mechanism 454 may reliably and/or predictably deform to the shape of crumpled state 448. Further, in some examples, compression mechanism 454 may be configured to repeatedly deform in response to distal force 456 and normal force 458 to compressed state 448 and thereinafter return to uncompressed state 446 once normal force 458 and/or distal force 456 is reduced or lifted (e.g., unapplied).

In some examples (not depicted), delivery device 450 may include one or more radiopaque elements configured to indicate an amount that compression mechanism 454 longitudinally compresses in response to a force above the threshold force. For example, similar to radiopaque markers elements 90 as depicted in FIG. 2A, delivery device 450 may include a first radiopaque element located adjacent a proximal portion of compression mechanism 454 and include a second radiopaque element adjacent a distal portion of compression mechanism 454. Using two such radiopaque elements, a clinician may track a compression of compression mechanism 454 from uncompressed state 446 to compressed state 448.

Figure 10B:
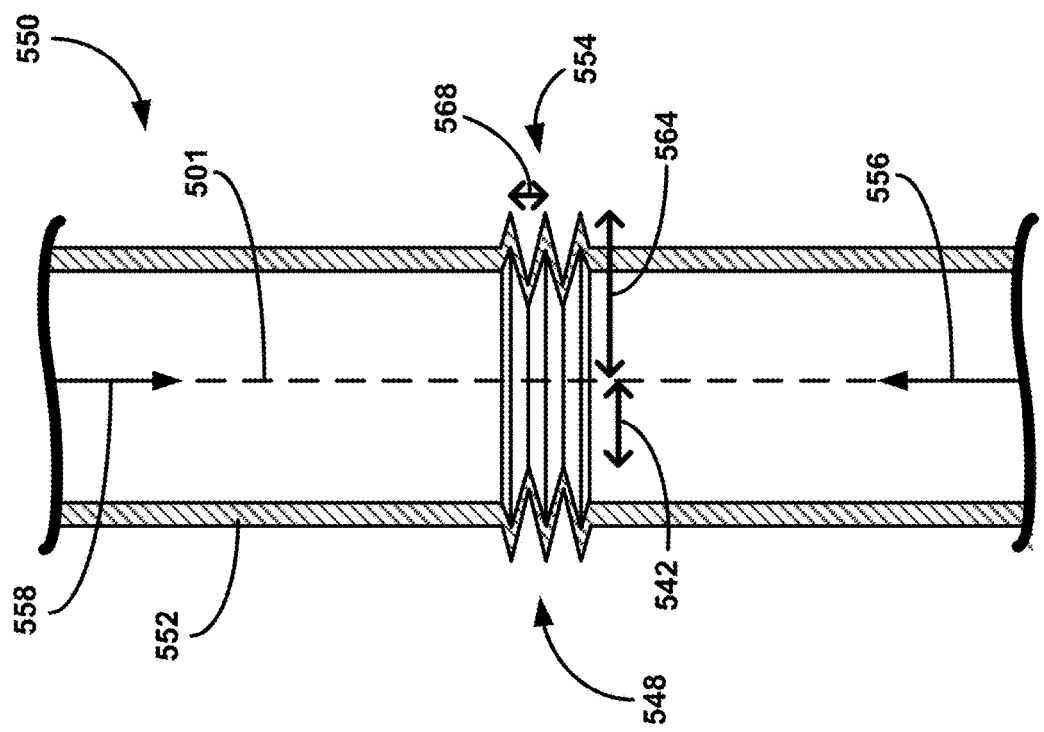
FIGS. 10A and 10B are conceptual and schematic diagrams illustrating cross-sectional views of an uncompressed and compressed state, respectively, of an example delivery device that includes an example compression mechanism that defines an accordion structure.
Figure 10A:
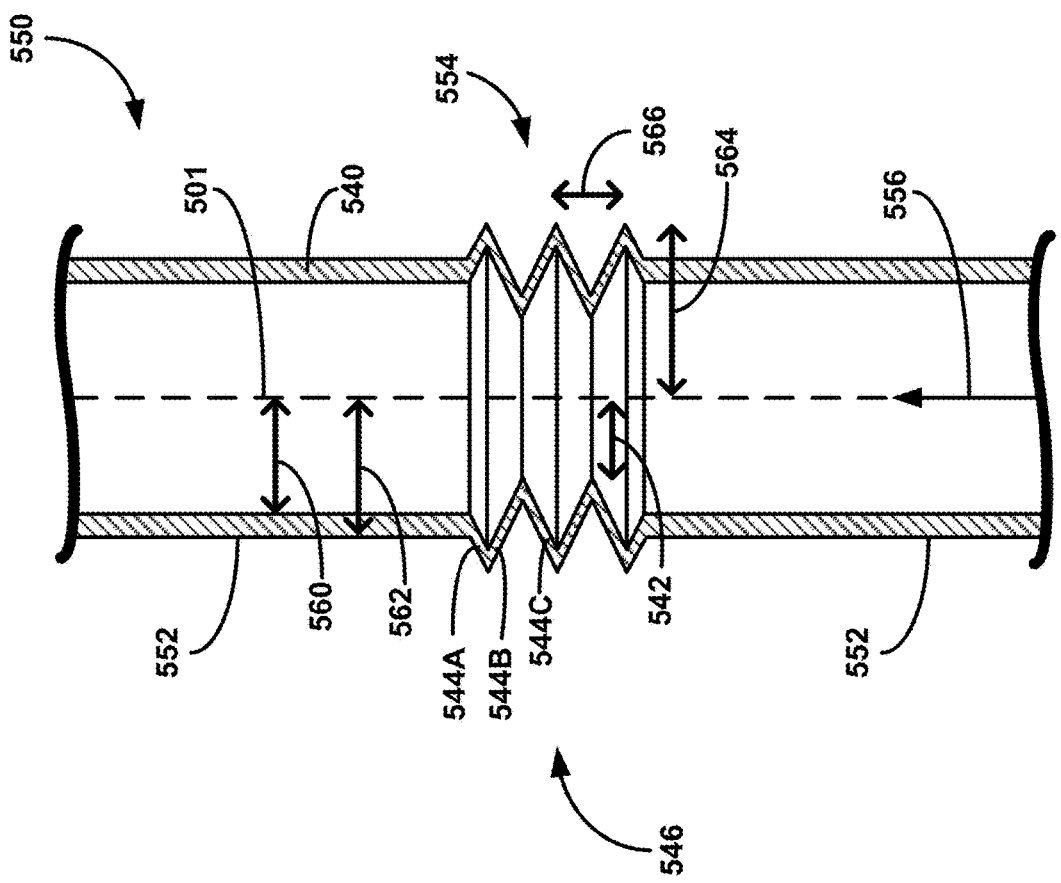

FIGS. 10A and 10B are conceptual and schematic diagrams of side views of an example medical delivery device 550 in uncompressed state 546 and compressed state 548. Delivery device 550 may be substantially similar to delivery device 50, delivery device 250, delivery device 350, and delivery device 450 except for any differences described herein. Delivery device 550 may define longitudinal axis 501 and may include deployment bay 552. Deployment bay 552 may be substantially similar to deployment bay 52, deployment bay 252, deployment bay 352, and/or deployment bay 452 except for any differences described herein.

Delivery device 550 includes compression mechanism 554, which may axially compress as described herein to provide similar utility as described above with regards to compression mechanism 54, compression mechanism 254, compression mechanism 354, and compression mechanism 454. As depicted in FIGS. 10A and 10B, delivery device 550 may include compression mechanism 554 within a length of deployment bay 552 (e.g., such that deployment bay 552 is on either axial side of compression mechanism 554). In other examples (not depicted), compression mechanism 554 may be at other locations along delivery device 550, such as immediately proximal to deployment bay 552 (e.g., similar to a depicted placement of compression mechanism 54 as on delivery device 50 in FIGS. 2A-6B), or at other locations along an elongated member of delivery device 550 (e.g., an elongated member similar to elongated member 62).

Compression mechanism 554 may define an accordion structure that includes panels that angle in towards and out away, e.g., alternatingly, from longitudinal axis 501. For example, along a length of deployment bay 552, deployment bay 552 may define tubular wall 540 that defines a substantially cylindrical shape that is centered on (e.g., coaxial with) longitudinal axis 501. Tubular wall 540 of deployment bay 552 may define a substantially constant internal radius 560 (as measured from longitudinal axis 501) and a substantially constant outer radius 562 along the length of deployment bay 552. Tubular wall 540 of deployment bay 552 may be attached to compression mechanism 554. In some examples, tubular wall 540 of deployment bay 552 and compression mechanism 554 may define a unitary structure.

Compression mechanism 554 may define a series of panels 544A-544C (collectively "panels 544"), where adjacent panels 544 are configured to extend at an angle relative to longitudinal axis 501 radially out from longitudinal axis 501 and then extend at an angle relative to longitudinal axis 501 radially in towards longitudinal axis 501. Panels 544 together may define an accordion structure that is centered on longitudinal axis 501. Panels 544 may extend between inner radius 542 and outer radius 564, where inner radius 542 is smaller than inner radius 560 of deployment bay 552 and outer radius 464 is larger than outer radius 562 of deployment bay 552. Further, in some examples tubular wall 540 may be relatively thicker than panels 544. In certain examples, compression mechanism 554 may be made of substantially the same materials as deployment bay 552.

Deployment bay 552 may be navigated to a target site (e.g., similar to target site 140 of FIGS. 4A-5B) by distal force 556 which may be substantially similar to distal force 156, distal force 256, distal force 356, and distal force 456. Once deployment bay 552 contacts a tissue layer of patient 14 at the target site, the tissue layer may apply normal force 558 to deployment bay 552 (and therein compression mechanism 554) as a result of ongoing distal force 556. Compression mechanism 554 may deform from uncompressed state 546 to compressed state 548 of FIG. 10B. In some examples, compressed state 548 of compression mechanism 554 may be predetermined.

For example, compressed state 548 of compression mechanism 554 as depicted in FIG. 10B may be predetermined, where panels 544 still extend radially in between inner radius 542 and outer radius 564 between different predetermined axial lengths between panels 544. As depicted in FIG. 10A, in uncompressed state 546, panels 544 may define axial length 566 between panels 544 extending out to greater radius 564. In compressed state 548, panels 544 may define axial length 568 between panels 544 extending out to greater radius 564. Further, in some examples, compression mechanism 554 may be configured to repeatedly deform in response to distal force 556 and normal force 558 to compressed state 548 and thereinafter return to uncompressed state 546 once normal force 558 and/or distal force 556 is reduced or lifted (e.g., unapplied).

In some examples (not depicted), delivery device 550 may include one or more radiopaque elements configured to indicate an amount that compression mechanism 554 longitudinally compresses in response to a force above the threshold force. For example, similar to radiopaque markers elements 90 as depicted in FIG. 2A, delivery device 550 may include a first radiopaque element located adjacent a proximal portion of compression mechanism 554 and include a second radiopaque element adjacent a distal portion of compression mechanism 554. Using two such radiopaque elements, a clinician may track a compression of compression mechanism 554 from uncompressed state 546 to compressed state 548.

Figure 11A:
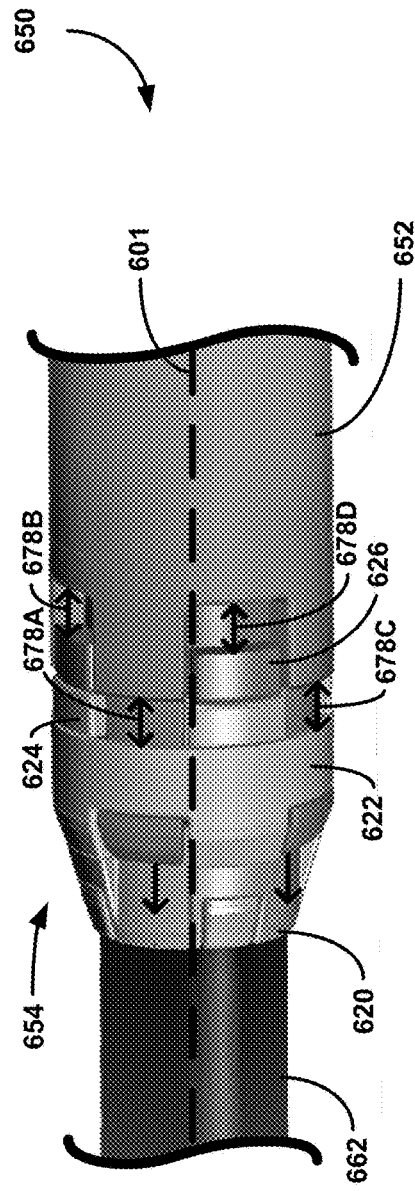
FIGS. 11A and 11B are conceptual and schematic diagrams illustrating a side view and exploded view, respectively, of an example delivery device that includes an example compression mechanism that includes a set of interlocking components.
Figure 11B:
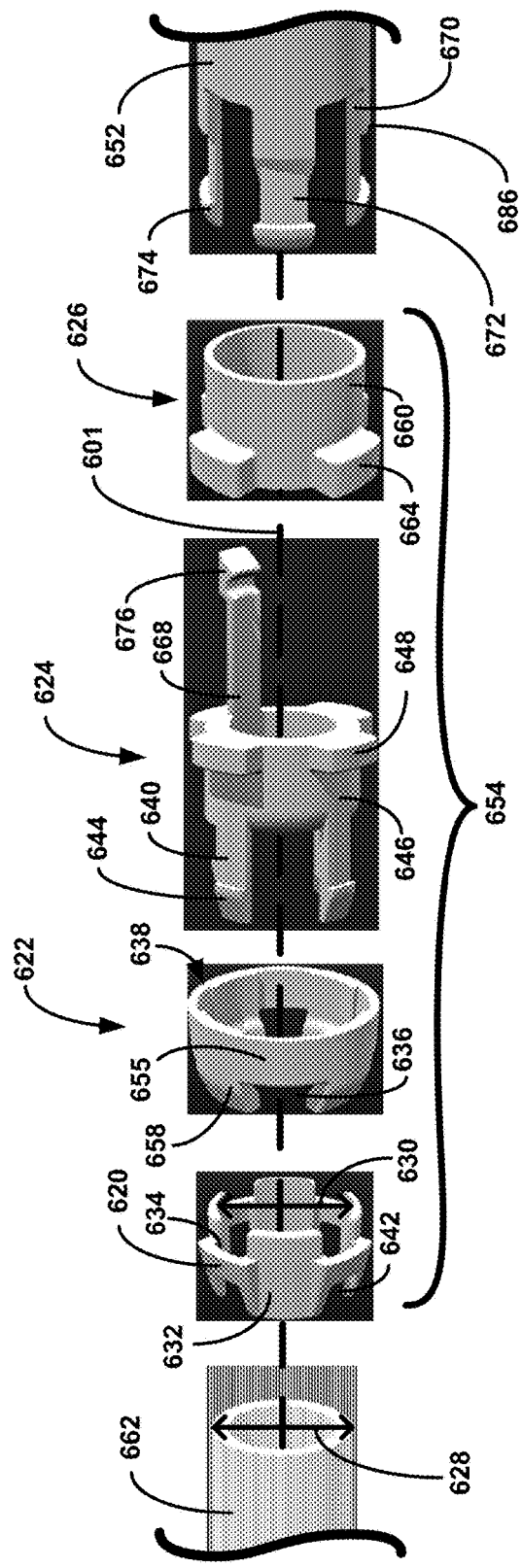

FIGS. 11A and 11B are conceptual and schematic diagrams illustrating a side view and exploded view, respectively, of an example delivery device 650 that includes an example compression mechanism 654 that includes a set of interlocking components. FIG. 11B depicts delivery device 650 exploded along longitudinal axis 601. Delivery device 650 may be substantially similar to delivery device 50, delivery device 250, delivery device 350, delivery device 450, and delivery device 650 except for any differences described herein. Delivery device 650 may define longitudinal axis 601 and may include deployment bay 652. Deployment bay 652 may be substantially similar to deployment bay 52, deployment bay 252, deployment bay 352, deployment bay 452, and deployment bay 552, except for any differences described herein. Delivery device 650 may further include elongated member 662. Elongated member 662 may be substantially similar to elongated member 62, with the exception of any differences described herein.

Delivery device 650 includes compression mechanism 654, which is configured to axially compress as described herein to provide similar utility as described above with regards to compression mechanism 54, compression mechanism 254, compression mechanism 354, compression mechanism 454, and compression mechanism 554. As depicted in FIGS. 11A and 11B, delivery device 650 may include compression mechanism 654 at a location immediately proximal to deployment bay 652. As such, compression mechanism 654 may be between elongated member 662 and deployment bay 652, therein substantially attaching elongated member 662 to deployment bay 652. In other examples (not depicted), compression mechanism 654 may be at other locations along delivery device 650, such as within a length of deployment bay 652 (e.g., similar to a depicted placement of compression mechanism 254, 354, 454, and 554 as on delivery device 250, 350, 450, and 550 in FIGS. 7A-10B), or at other locations along 662 elongated member of delivery device 650.

Compression mechanism 654 may define a set of interlocking components that are configured to securely attach to both elongated member 662 and deployment bay 652 and enable deployment bay 652 to axially move relative to elongated member 662 in response to a force above a threshold force. For example, compression mechanism 654 may include interlocking components proximal cap 620, ring member 622, intermediate member 624, and distal cap 626. Proximal cap 620 may be securely attached to elongated member 662. For example, intermediate member 624 may be molded directly to elongate member 662. Ring member 622, proximal cap 620, distal cap 626, distal cap 626, and deployment bay 652 may all be configured to interlock/snap together to intermediate member 624.

Distal cap 626 may be configured to compress in response to a force over the threshold force. Distal cap 626 may longitudinally compress relatively more than other components of delivery device 650 in response to the force above the threshold force, such that functionally distal cap 626 is the only component to longitudinally compress. Distal cap 626 may compress as a result of a relative softness of a material of distal cap 626, such that distal cap 626 may be relatively softer than other components of compression mechanism 654 as well as softer than elongated member 662 and deployment bay 652. Compression mechanism 654 may define a plurality of gaps 678A-678D (collectively "gaps 678) between respective interlocking components.

In some examples, compression mechanism 654 may be configured to define gaps 678 into which deployment bay 652 may axially slide. Deployment bay 652 may axially slide in gaps 678 relative to components of compression mechanism 654 and relative to elongated member 662. Deployment bay 652 may slide in gaps 678 in response to distal cap 626 compressing.

In some examples, one member of compression mechanism 654 may be securely attached to elongate member 662 in a semi-permanent manner (e.g., such as overmolded on, chemically bonded to, or the like), while other components are interlocked/snapped into position to the one member that is securely attached to elongate member 662. For example, intermediate member 624 may be configured to be securely attached to elongated member 662. In some examples, intermediate member 624 may be secured to elongated member 662 by being molded directly to an outer distal surface of elongated member 662, such that outer diameter 628 of elongated member 662 is substantially the same as an inner diameter 630 of intermediate member 624. In some examples, at least a portion of central barrel 646 of intermediate member 624 and proximally extending connection members 640 of intermediate member 624 may be molded to elongate member 662. In other examples, a distal end of elongated member 662 may be chemically or heat bonded to an inner surface of intermediate member 624. Intermediate member 624 may define a lumen that is substantially centered on longitudinal axis 601 of delivery device 650. In some examples, intermediate member 624 may define a substantially circular "hollow" shape as a result of this lumen.

Intermediate member 624 may define features to which other features of compression mechanism 654 may be secured. For example, proximally extending connection members 640 of intermediate member 624 may proximally terminate in interlock lips 644 that radially extend out from longitudinal axis 601 of delivery device 650. In some examples, intermediate member 624 may define a plurality of connection members 640 and a plurality of interlock lips 644 as depicted in FIGS. 11A and 11B. For example, intermediate member 624 may define four connection members 640 and four interlock lips 644 that are radially spaced out around longitudinal axis 601. Further, intermediate member 624 may define one or more flanges 648 that extend radially out from barrel 646. Flanges 648 may be located on intermediate member 624 toward a distal end of barrel 646. Flanges 648 may be radially arranged around intermediate member 624. For example, intermediate member 624 may include four flanges 648 that are each mirrored across longitudinal axis 601 from each other. Each flange 648 may only extend partway around a perimeter of barrel 646, such that gaps are present between radially adjacent flanges 648. In some examples, each flange 648 may be axially aligned with a respective connection member 640, such that each flange 648 is on a distal end of barrel 646 opposite a respective connection member 640.

Intermediate member 624 may define a substantially circular cross-section. Further, intermediate member 624 may be substantially symmetrical as viewed along planes that intersect with and are parallel with the longitudinal axis 601 of the delivery device 650. Where intermediate member 624 includes a plurality of connection members 640, interlock lips 644, and/or flanges 648, the plurality of connection members 640, interlock lips 644, and/or flanges 648 may be radially arranged around longitudinal axis 601. Put differently, where there are more than one of any of connection members 640, interlock lips 644, and/or flanges 648, such elements may be mirrored or otherwise evenly spaced around longitudinal axis 601 of delivery device 650.

In some examples intermediate member 624 may further include distally extending deployment member 668. Deployment member 668 may be configured to secure a medical device within deployment bay 652 until compression mechanism 654 compresses, at which point deployment member 668 may deploy the medical device. For example, deployment member 668 may flex in response to compression mechanism 654 compressing, therein deploying a medical device. Distally extending deployment member 668 may axially extend in a distal direction that is substantially parallel with longitudinal axis 601 from barrel 646 of intermediate member 624. In some examples, intermediate member 624 may only define one distally extending deployment member 668, though in other examples intermediate member 624 may define a plurality of distally extending deployment members 668. Distally extending connecting member 668 may define ridge 676 that extends radially out from a distal portion of distally extending deployment member 668. Ridge 676 may initially be coupled to a medical device within deployment bay 652 to secure the medical device, and may become uncoupled to the medical device in response to compression mechanism 654 compressing.

Proximal cap 620 may be configured to be securely interlocked to intermediate member 624 as intermediate member is fixedly attached to elongate member 620. Toward this end, proximal cap 620 may define one or more notches 634 that extend radially out from inner radius 630 of proximal cap 620 longitudinally along a length of proximal cap. Further, proximal cap 620 may define one or more troughs 632 that extend radially into proximal cap 620 longitudinally along a length of proximal cap. In some examples, proximal cap 620 may define a plurality of troughs 632 and a plurality of notches 634 as depicted in FIGS. 11A and 11B. For example, proximal cap 620 may define four troughs 632 and four notches 634. In some examples, troughs 632 and notches 634 may be radially adjacent to each other, such that troughs 632 and notches 634 substantially do not radially overlap. In some examples, respective portions of proximal cap 620 that define one or more troughs 632 may axially extend in a proximal direction relative to respective portions of proximal cap 620 that define one or more notches 634. As a result of this relative proximal extension, notches 634 may proximally terminate at radial openings 642 that are at least partially defined by radially adjacent troughs 632.

Proximal cap 620 may be configured to slide notches 634 over interlock lips 644, after which interlock lips 644 may extend radially out through respective openings 642. Upon extending radially out from respective openings, interlock lips 644 may axially interface with proximal cap 620, such that interlock lips 644 mechanically secure proximal cap 620 to stop proximal cap 620 from proximally moving relate to intermediate member 624 (and therein elongated member 662 which is fixedly attached to intermediate member 624). Proximal cap 620 may define a lumen that is substantially centered on longitudinal axis 601 of delivery device 650. In some examples, proximal cap 620 may define a substantially circular "hollow" shape as a result of this lumen. The lumen of proximal cap 620 may be substantially coaxial with the lumen of intermediate member 624 as the two are interlocked on delivery device 650.

Proximal cap 620 may define a substantially circular cross-section. Further, proximal cap 620 may be substantially symmetrical as viewed along planes that intersect with and are parallel with the longitudinal axis 601 of the delivery device 650. Where proximal cap 620 includes a plurality of troughs 632 and or notches 634, the plurality of troughs 632 and/or notches 634 may be radially arranged around longitudinal axis 601. Put differently, where there are more than one of either or both troughs 632 and/or notches 634, troughs 632 and/or notches 634 may be mirrored or otherwise evenly spaced around longitudinal axis 601 of delivery device 650.

Ring member 622 may include substantially circular band 655 with a plurality of extending members 658 that proximally extend from band 655 axially in a direction that is substantially parallel to longitudinal axis 601. Ring member 622 may be configured to be secured on barrel 646 of intermediate member 624 between flanges 648 and distal-facing surfaces defined by notches 634. Put differently, an internal diameter of ring member 622 may be substantially similar to an outer diameter of barrel 646 of intermediate member 624 such that ring member 622 may be initially slide over barrel 646 before interfacing with and being secured from proximal movement by distal-facing surfaces of notches 634 of proximal cap 620 and being secured from distal movement by proximal-facing surfaces of flanges 648.

Ring member 622 may define one or more radial openings 636. Radial openings 636 may be substantially similar to openings 642. Each respective opening 636 may be defined by a portion of a proximal surface of band 655 and two radially adjacent extending members 658. In some examples, extending members 658 (and therein openings 636) may be radially arranged around ring member 622. For example, ring member 622 may define four extending member 658 (and therein four openings 636 between adjacent pairs of extending members 658), wherein each extending member 658 is mirrored across longitudinal axis 601 by another extending member 658. In some examples, as extending members 658 extend axially in a proximal direction from band 655, extending member 658 may curl or deflect radially in towards longitudinal axis 601. Ring member 622 may define openings 636 such that each opening 636 may be aligned with a respective trough 632 of proximal cap 620 when ring member 622 is secured to intermediate member 624 and proximal cap 620.

Ring member 622 may define one or more notches 638 that extend radially out from an inner radius of band 655 of ring member 622. Ring member 622 may define notches 638 to axially align with openings 636. For example, each notch 638 may axially extend across band 655 distal to a respective opening 636.

Ring member 622 may define a lumen that is substantially centered on longitudinal axis 601 of delivery device 650. In some examples, ring member 622 may define a substantially circular "hollow" shape as a result of this lumen. The lumen of ring member 622 may be substantially coaxial with the lumens of proximal cap 620 and intermediate member 624 as the three are interlocked on delivery device 650 (e.g., as ring member 622 and proximal cap 620 are interlocked with intermediate member 624 which is fixedly secured to elongate member 662).

Distal cap 626 may include barrel 660 and one or more flanges 664 that extend radially out from barrel 660 at a proximal end of barrel 660. Distal cap may be configured to slide over distally extending connecting member 668. An axial length of distal cap 626 may be substantially similar to an axial length between barrel 646 and ridge 676 of distally extending connecting member 668, such that when distal cap 626 is flush with intermediate member 624 ridge 676 maintains distal cap 626 flush with intermediate member 624.

Flanges 664 may be substantially similar to flanges 648 of intermediate member 624. In some examples, flanges 664 of distal cap 626 may be configured to be aligned with flanges 648 of intermediate member 624 when distal cap 626 is secured to intermediate member 624 (e.g., secured via ridge 676). For example, similar to flanges 648 of intermediate member 624, each flange 664 may be mirrored across longitudinal axis 601 with another respective flange 664. Each flange 664 may extend partway around a perimeter of barrel 660, such that gaps are present between radially adjacent flanges 664.

As described above, distal cap 626 may be made of a relatively softer material than other components of compression mechanism 654 and/or delivery device 650. In some examples, both barrel 660 and flanges 664 of distal cap 626 may be made of the relatively softer material. In other examples, only barrel 660 (or only a distal portion of barrel 660) may be made of the relatively softer material.

Distal cap 626 may define a lumen that is substantially centered on longitudinal axis 601 of delivery device 650. In some examples, distal cap 626 may define a substantially circular "hollow" shape as a result of this lumen. The lumen of distal cap 626 may be substantially coaxial with the lumens of proximal cap 620, ring member 622, and intermediate member 624 as the four are interlocked on delivery device 650.

A proximal end of deployment bay 652 may be configured to slide over barrel 660. Deployment bay 652 may include proximally extending fingers 670 that extend axially in a proximal direction from deployment bay 652. Each extending finger 670 may define depression 672 that extends radially in to extending finger at proximal portion of extending finger 670 between proximal lip 674 and distal lip 686. Once distal cap 626 is received by deployment bay 624, extending fingers 670 may be configured to axially extend within gaps between flanges 664 and flanges 648. Once extending fingers 670 have axially extending between flanges 664, 648 of distal cap 626 and intermediate member 624, ring member 622 may be received by depression 672 of extending fingers 670. Once received, extending members 658 may extend proximally to curl around proximal lips 674 of extending fingers 670 to interface with ring member 622 to stop deployment bay 652 from distal movement relative to ring member 622 when distal cap 626 is uncompressed. As distal cap 626 compresses, deployment bay 652 may longitudinally move into gaps 678 defined by compression mechanism 654 until distal lips 686 interface with a distal-facing surface of ring member 622. In this way, elongated member 662 may be securely attached to intermediate member 624 which is interlocked with proximal cap 620, distal cap 626, ring member 622, and deployment bay 652, such that substantially only deployment bay 652 may move proximally relative to other components of delivery device 650 in response to distal cap 626 compressing in response to a force above the threshold force.

FIGS. 12A and 12B depict conceptual and schematic diagrams of a cross-sectional views taken along a cut plane through longitudinal axis 601 of delivery device 650 when distal cap 626 is in an uncompressed state and a compressed state, respectively. As depicted in FIG. 12A, proximal lips 674 of extending fingers 670 of deployment bay 652 are interfacing with ring member 622 while compression mechanism 654 defines gaps 678. Further, as depicted in FIG. 12A, distal cap 626 is uncompressed, such that distal cap 626 defines first axial length 690. Comparatively, as depicted in FIG. 12B, distal cup 626 has compressed to a second axial length 692 that is relatively less than the first axial length 690. Distal cap 626 may compress in response to distal force 656 that is greater than a threshold force. Distal force 656 may be substantially similar to distal force 156, distal force 256, distal force 356, distal force 456, and distal force 556. In response to distal force 656 compressing distal cap 626, deployment bay 652 may extend proximally into gaps 678 to substantially occupy/eliminate gaps 678. Deployment bay 652 may extend proximally into gaps 678 until distal lip 686 of extending fingers 670 interfaces with distal-facing surface of ring member 622. In this way, a longitudinal length of gaps 678 may define an amount which distal cap 626 compresses, as distal force 656 may only compress distal cap 626 a longitudinal amount that is equal to a length that deployment bay 652 may proximally move as defined by gaps 678. Though FIG. 12B depicts distal cap 626 compressing substantially without buckling radially inward for purposes of clarity, in other examples distal cap 626 may buckle inward towards a longitudinal axis 601 of delivery device 650 in response to distal force 656.

FIGS. 12A and 12B depict circular groove 682 defined by deployment bay 652. Circular groove 682 may be a groove that cuts axially into an internal surface of deployment bay 652. In some examples, circular groove 682 may define a substantially constant radius 684 from longitudinal axis 601 as circular groove 682 cuts axially into deployment bay 652. Deployment bay 652 may define groove 682 at an axial location that is substantially aligned with a distal end of fingers 670 of deployment bay 652, such that, as received by deployment bay 652, distal cap 626 may extend distally substantially up to a distal terminus of each of the fingers 670.

Distal end 680 of distal cap 626 may be received within circular groove 682 of deployment bay 652 to radially and axially secure distal cap 626 to deployment bay 652. Deployment bay 652 may define circular groove 682. In some examples, circular groove 682 may extend 360° around longitudinal axis 601 of delivery device 650. In other examples, circular groove 682 may only extend around longitudinal axis 601 an amount that corresponds to a shape defined by distal end 680 of distal cap 626.

In some examples (not depicted), delivery device 650 may include one or more radiopaque elements configured to indicate an amount that compression mechanism 646 longitudinally compresses in response to a force above the threshold force. For example, similar to radiopaque markers elements 90 as depicted in FIG. 2A, delivery device 650 may include a first radiopaque element attached to one or more of elongated member 662, proximal cap 620, ring member 622, intermediate member 624, and/or distal cap 626, and include a second radiopaque element attached to deployment bay 652. Using two such radiopaque elements, a clinician may track a compression of compression mechanism 654 from an uncompressed state to a compressed state.

Alternatively, or additionally, a delivery device may include electrical components that may indicate when a compression mechanism compresses in response to a force above the threshold force. For example, a delivery device may include an electrical circuit that closes or opens in response to the deformation in response to the force above the threshold force. For example, delivery device 650 may include electrical components of an electrical circuit on opposing sides of one or more gaps 678, such that components may contact each other (and therein close the loop) or separate (and therein open the loop) as members of compression mechanism 654 move into gaps 678. The electrical circuit may be configured to provide an indication to a clinician handling delivery device when the electrical loop is thusly partially and/or fully closed or opened. For example, the electrical circuit may be configured to turn an indicator such as a light emitting diode (LED), a haptic feedback device, or the like on or off in response to the electric circuit being opened or closed. A strength of the indication (e.g., the amount of light provided by the LED or the amount of haptic feedback) may indicate an extent to which the electrical is currently open and/or closed and/or close to being opened or closed. This indicator may be located near a proximal end of delivery device 650 (e.g., such as near or on a hub 56 as depicted in FIG. 2A) to improve an ability of the clinician detecting the indication.

Figure 13B:
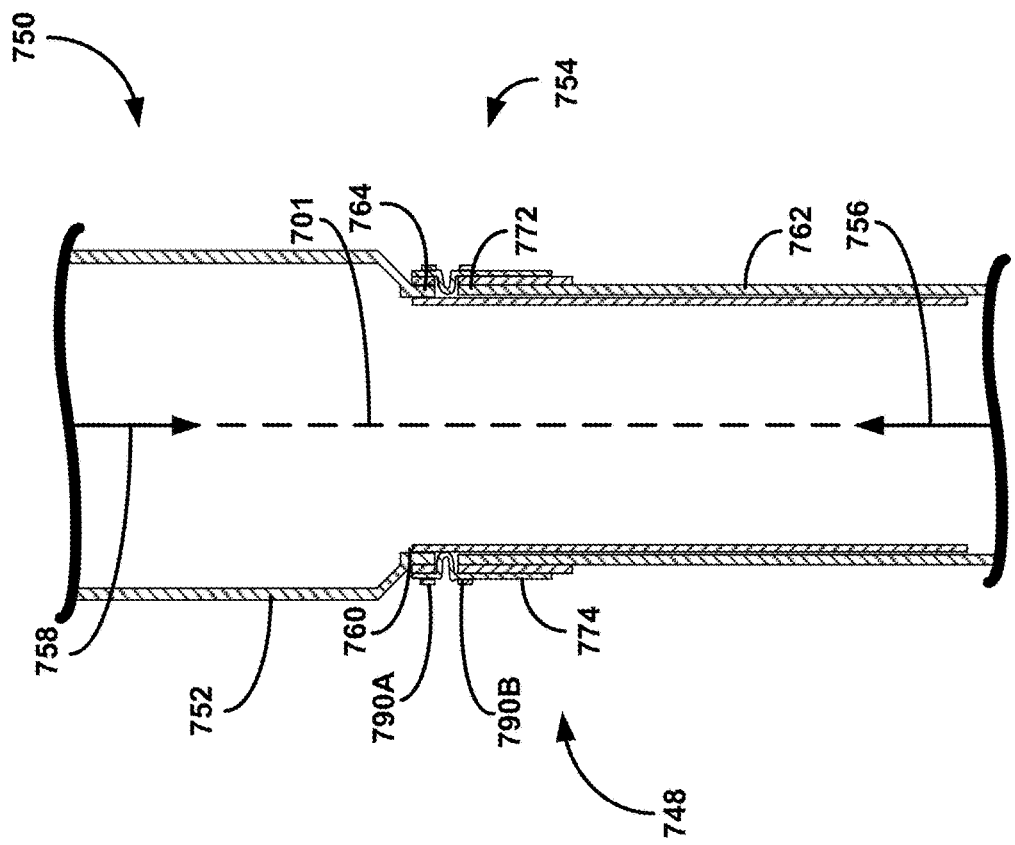
FIGS. 13A and 13B are conceptual and schematic diagrams illustrating cross-sectional views of an uncompressed and compressed state, respectively, of an example delivery device that includes an example compression mechanism that defines an internal slide.
Figure 13A:
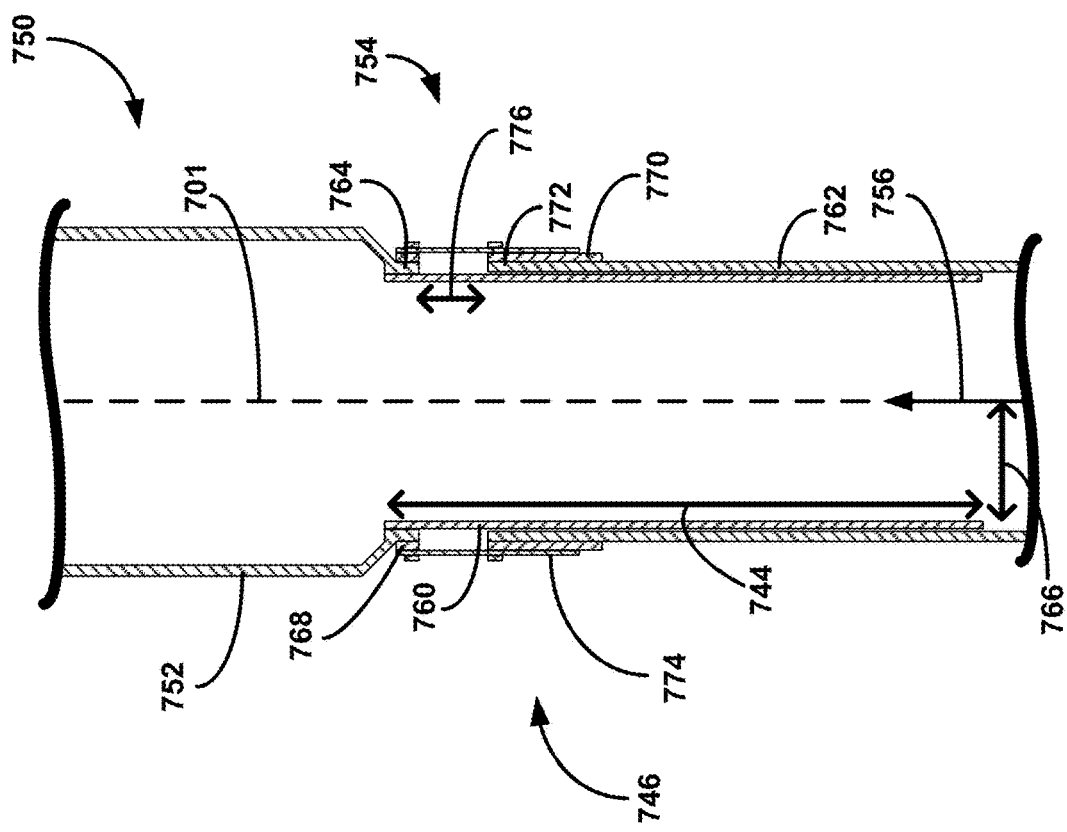

FIGS. 13A and 13B are conceptual and schematic diagrams of side views of an example medical delivery device 750 in uncompressed state 746 and compressed state 748, respectively. Delivery device 750 may be substantially similar to delivery device 50, delivery device 250, delivery device 350, delivery device 450, delivery device 550, and delivery device 650, except for any differences described herein. Delivery device 750 may define longitudinal axis 701 and may include deployment bay 752 and elongated member 762. Deployment bay 752 may be substantially similar to deployment bay 52, deployment bay 252, deployment bay 352, deployment bay 452, deployment bay 552, and/or deployment bay 652 except for any differences described herein. Similarly, elongated member 762 may be substantially similar to elongated member 62 and/or elongated member 662 except for any differences described herein.

Delivery device 750 includes compression mechanism 754, which may axially compress as described herein to provide similar utility as described above with regards to compression mechanism 54, compression mechanism 254, compression mechanism 354, compression mechanism 454, compression mechanism 554, and compression mechanism 654. As depicted in FIGS. 13A and 13B, delivery device 750 may include compression mechanism 754 at a location immediately proximal to deployment bay 752 (e.g., such that deployment bay 752 is immediately distal to compression mechanism 754 and elongated member 762 is immediately proximal to compression mechanism 754). In other examples (not depicted), compression mechanism 754 may be at other locations along delivery device 750, such as within a length of deployment bay 552 (e.g., similar to a depicted placement of compression mechanism 254, 354, 454, and 554 as on delivery device 250, 350, 450, and 550 in FIGS. 7A-10B), or at other locations along elongated member 762 of delivery device 750.

Compression mechanism 754 may define tubular slide 760 that is configured to secured to deployment bay 752 and configured to axially slide relative to elongated member 760. Tubular slide 760 may be a member that is substantially tubular in shape and attached to an internal circumference of proximal portion 764 of deployment bay 752. Tubular slide 760 may be aligned (substantially coaxial with) longitudinal axis 701 of delivery device 750. Tubular slide 760 may define relatively constant internal radius 766 along axial length 744 of tubular slide 760. Internal radius 766 may be only slightly smaller than an internal radius of elongated member 762.

Compression mechanism 754 may further include distal collar 768 secured to an outer circumference of proximal portion 764 of deployment bay 752, proximal collar 770 secured to outer circumference of distal portion 772 of elongated member 762, and flexible sheath 774 secured to an outer circumference of both proximal and distal collar 770, 768. Flexible sheath 774 may be relatively flexible relative to other components of compression mechanism 754 (e.g., tubular slide 760, proximal collar 770, and/or distal collar 768). For example, flexible sheath 774 may be made of a relatively flexible material, or flexible sheath 774 may be relatively thinner than other components of compression mechanism 754. Flexible sheath 774 may be the only component of compression mechanism 754 that is secured to both deployment bay 752 and elongated member 762. Flexible sheath 774 may couple deployment bay 752 to elongated member 762 such that deployment bay 752 and elongated member 762 define axial gap 776 between them when compression mechanism 754 is in uncompressed state 746. In some examples, axial length 744 may be substantially larger than axial gap 776 in uncompressed state 746 and is secured to deployment bay 752 such that tubular slide 760 axially extends well past distal portion 772 of elongated member 762. For example, tubular slide 760 may be secured to deployment bay 752 and define axial length 744 such that at least half of axial length 744 of tubular slide 760 extends proximally past a distal end of elongated member 762. In some examples, tubular slide 760 may extend substantially all the way back to a hub of delivery device 750, at which proximal location tubular slide 760 may be locked to reduce a possibility of premature deployment of the medical device and/or protect the structural integrity of the compression mechanism 754 as the compression mechanism 754 is inserted through an introducer sheath. In such examples, compression mechanism 754 may function primarily as a coil spring or the like. Configuring tubular slide 760 to extend proximally well past the distal end of elongated member 762 may improve an ability of delivery device 750 to maintain a predetermined shape as delivery device 750 is handled and navigated intravenously.

Deployment bay 752 may be navigated to a target site (e.g., similar to target site 140 of FIGS. 4A-5B) by distal force 756 which may be substantially similar to distal force 156, distal force 256, distal force 356, distal force 456, distal force 556, and distal force 656. Once deployment bay 752 contacts a tissue layer of patient 14 at the target site, the tissue layer may apply normal force 758 to deployment bay 752 (and therein compression mechanism 754) as a result of ongoing distal force 756. Compression mechanism 754 may deform from uncompressed state 746 to compressed state 748 of FIG. 13B. In some examples, compressed state 748 of compression mechanism 754 may be predetermined.

In some examples, compression mechanism 754 may include radiopaque elements such as radiopaque bands 790A, 790B (collectively "radiopaque bands 790"). Both radiopaque bands 790 may be secured to an outer circumference of flexible sheath 774. For example, compression mechanism 754 may include proximal radiopaque band 790B that is radially aligned with distal portion 772 of elongated member 762 and distal radiopaque band 790A that is radially aligned with proximal portion 764 of deployment bay 752. A clinician may monitor an axial distance between radiopaque bands 790 to determine when compression mechanism 754 defines compressed state 748, and therein a housed medical device is ready to be deployed from deployment bay 752.

Figure 14B:
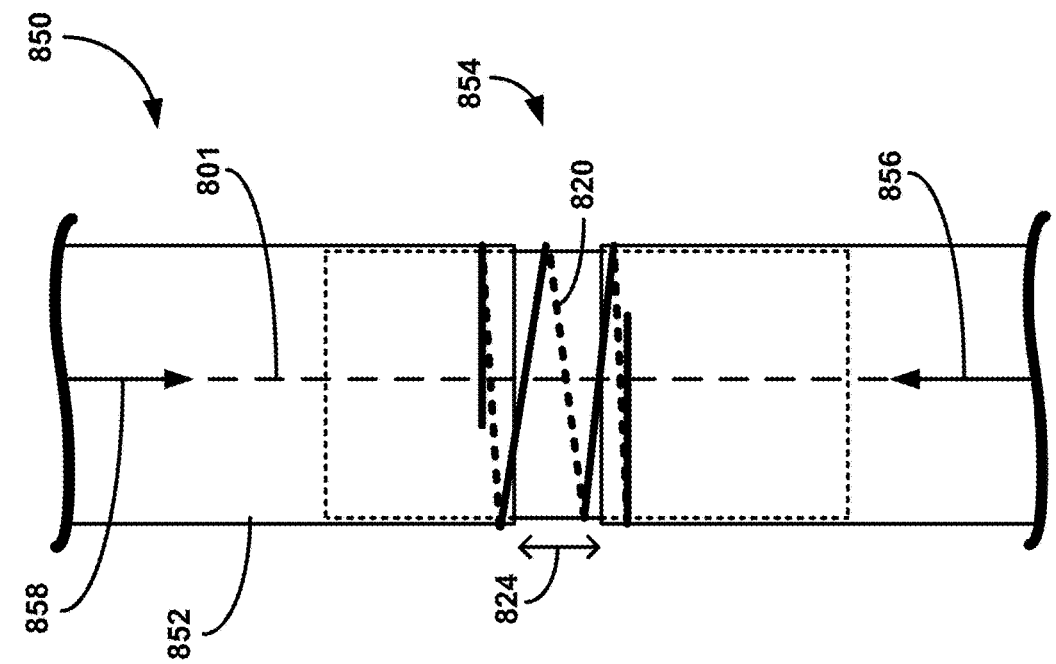
FIGS. 14A and 14B are conceptual and schematic diagrams illustrating cross-sectional views of an uncompressed and compressed state, respectively, of an example delivery device that includes an example compression mechanism that defines a spring structure.
Figure 14A:
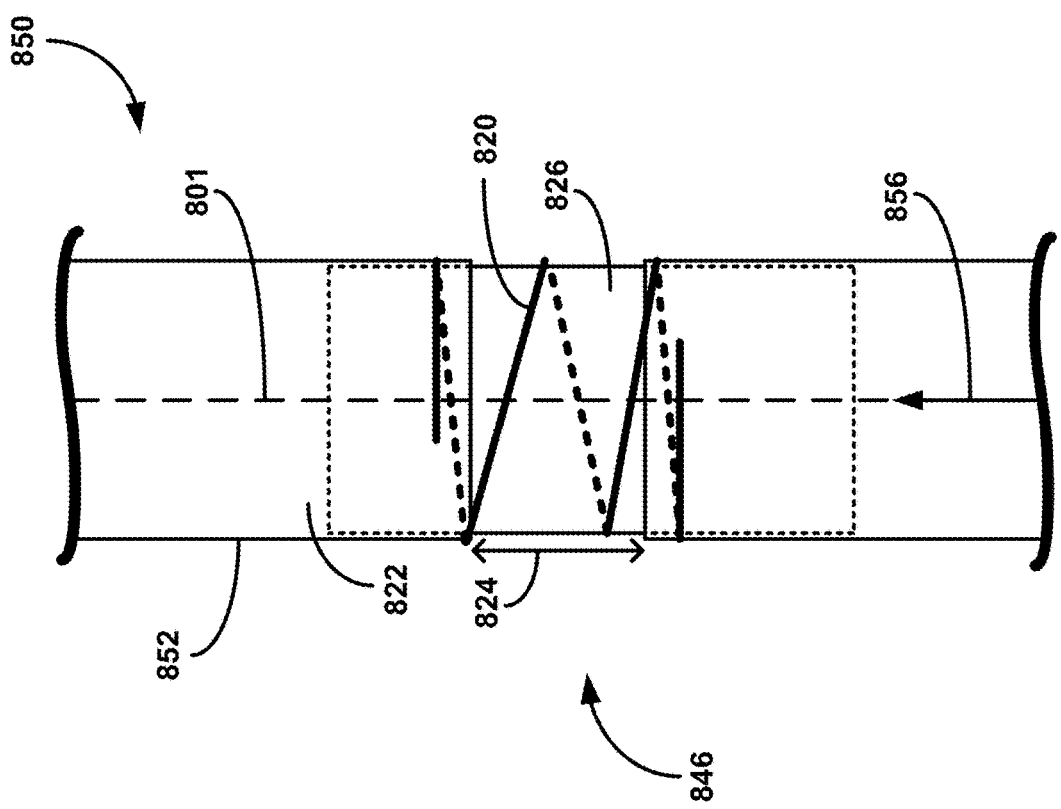

FIGS. 14A and 14B are conceptual and schematic diagrams of side views of an example medical delivery device 850 in uncompressed state 846 and compressed state 848, respectively. Delivery device 850 may be substantially similar to delivery device 50, delivery device 250, delivery device 350, delivery device 450, delivery device 550, delivery device 650, and delivery device 750 except for any differences described herein. Delivery device 850 may define longitudinal axis 801 and may include deployment bay 852. Deployment bay 852 may be substantially similar to deployment bay 52, deployment bay 252, deployment bay 352, deployment bay 452, deployment bay 552, deployment bay 652, and/or deployment bay 752 except for any differences described herein.

Delivery device 850 includes compression mechanism 854, which may be configured to axially compress as described herein to provide similar utility as described above with regards to compression mechanism 54, compression mechanism 254, compression mechanism 354, compression mechanism 454, compression mechanism 554, compression mechanism 654, and/or compression mechanism 754. As depicted in FIGS. 14A and 14B, delivery device 850 may include compression mechanism 854 within a length of deployment bay 852 (e.g., such that deployment bay 852 is on either axial side of compression mechanism 854). In other examples (not depicted), compression mechanism 854 may be at other locations along delivery device 850, such as immediately proximal to deployment bay 852 (e.g., similar to a depicted placement of compression mechanism 54 as on delivery device 50 in FIGS. 2A-6B), or at other locations along an elongated member of delivery device 850 (e.g., an elongated member similar to elongated member 62).

Compression mechanism 854 may define a spring structure that includes an external spring 820 that is secured to outer surface 822 of deployment bay 852 on either longitudinal side of gap 824 in deployment bay 852. Spring 820 may wrap around deployment bay 852 as spring 820 longitudinally extends across gap 824. Compression mechanism 854 may include internal slide 826 that extends across gap 824 within deployment bay 852. Slide 826 may be secured to only one side of deployment bay 852 relative to gap 824, such that the slide 826 may longitudinally move relative the other side of deployment bay 852. Slide 826 may define a length within deployment bay 852 sufficient to keep both sides of deployment bay 852 across gap 824 centered on longitudinal axis 801. For example, slide 826 may define a length that is 75% or more the length of deployment bay 852. Slide 826 may be made of substantially the same materials as deployment bay 852. Spring 820 may be secured (e.g., welded) to deployment bay on either side of gap 824. Spring 820 may be unsecured across gap 824, such that spring 820 is free to compress across gap 824. Spring 820 may be centered on longitudinal axis 801.

Deployment bay 852 may be navigated to a target site (e.g., similar to target site 140 of FIGS. 4A-5B) by distal force 856 which may be substantially similar to distal force 156, distal force 256, distal force 356, distal force 456, distal force 556, distal force 656, and distal force 756. Once deployment bay 852 contacts a tissue layer of patient 14 at the target site, the tissue layer may apply normal force 858 to deployment bay 852 (and therein compression mechanism 854) as a result of ongoing distal force 856. Compression mechanism 854 may deform from uncompressed state 846 to compressed state 848 of FIG. 14B. In some examples, compressed state 848 of compression mechanism 854 may be predetermined.

For example, compressed state 848 of compression mechanism 854 as depicted in FIG. 14B may be predetermined, such that spring 820 compresses a predetermined amount in response to distal force 856 and normal force 858. As a result of spring 820 compressing, gap 824 within deployment bay 852 may compress a predetermined amount, therein decreasing an overall length of deployment bay 852. Further, in some examples, compression mechanism 854 may be configured to repeatedly deform in response to distal force 856 and normal force 858 to compressed state 848 and thereafter return to uncompressed state 846 once normal force 858 and/or distal force 856 is reduced or lifted (e.g., unapplied).

In some examples (not depicted), delivery device 850 may include one or more radiopaque or echogenic elements configured to indicate an amount that compression mechanism 854 longitudinally compresses in response to a force above the threshold force. For example, similar to radiopaque markers elements 90 as depicted in FIG. 2A, delivery device 850 may include a first radiopaque element located adjacent a proximal portion of compression mechanism 854 and include a second radiopaque element adjacent a distal portion of compression mechanism 854. Using two such radiopaque elements, a clinician may track a compression of compression mechanism 854 from uncompressed state 846 to compressed state 848.

Figure 15:
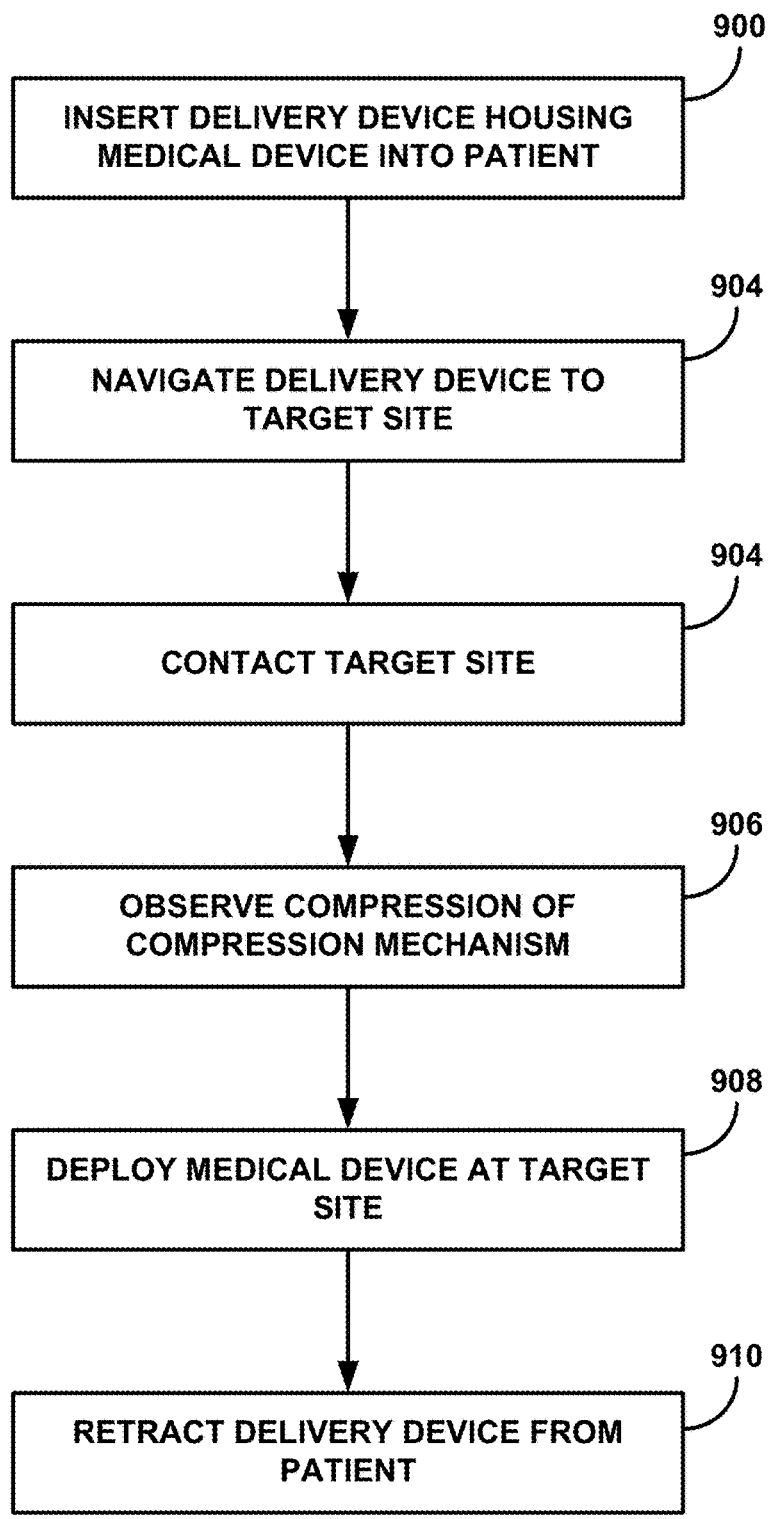
FIG. 15 depicts a flowchart of a method of delivering a medical device to a target site within a patient using a delivery device.

FIG. 15 depicts a flowchart of a method of delivering a medical device to a target site within a patient using a delivery device as described herein. FIG. 15 is discussed with reference to delivery device 50 of FIGS. 2A-6B as well as IMD 16A of FIG. 1A, but it is to be understood that the method of FIG. 15 may be completed using the other delivery device described herein to delivery any insertable or implantable medical device in other examples. A clinician may insert delivery device 50 into patient 14 (900). IMD 16A may be housed in deployment bay 52 of delivery device 50 when delivery device 50 is inserted into patient. A clinician may insert delivery device 50 into patient 14 using an introducer sheath.

A clinician may navigate delivery device 50 to target site 140 within patient 14 (902). For example, a clinician may navigate deployment bay 52 delivery device 50 to right atrium 20 of heart 12 of patient 14 (as depicted in FIG. 1A). The clinician may navigate delivery device 50 to the target site using one or more deflection member 86A, 86B using hub 56. Once the clinician has navigated deployment bay 52 to target site 140, the clinician may press deployment bay 52 against the target site 140 (904). The clinician may press deployment bay 52 against target site 140 with distal force 156 that is above a threshold, such that target site 158 applies a longitudinal normal force 158 on deployment bay 52. Distal force 156 applied by the clinician may be less that a force that perforates tissue layer 142 with distal end 162 of deployment bay 52.

The clinician may observe compression mechanism 54 of delivery device 50 compressing in response to the clinician applying distal force 156 that is above the threshold force (906). Compression mechanism 54 may compress such that elongated member 62 of delivery device 50 longitudinally moves toward deployment bay 52 of delivery device 50. The clinician may observe compression mechanism 54 compressing using fluoroscopy techniques to monitor one or more radiopaque bands of delivery device 50. In response to observing compression mechanism 54 compressing a predetermined amount, the clinician may deploy IMD 16A (808). The clinician may deploy IMD 16A such that fixation element 17 extends distally out of distal opening 70 of deployment bay 52. Once IMD 16A is deployed, the clinician may retract delivery device 50 out of patient (910). The clinician may withdraw delivery device 50 out of introducer sheath through which delivery device 50 was inserted.

Figure 16:
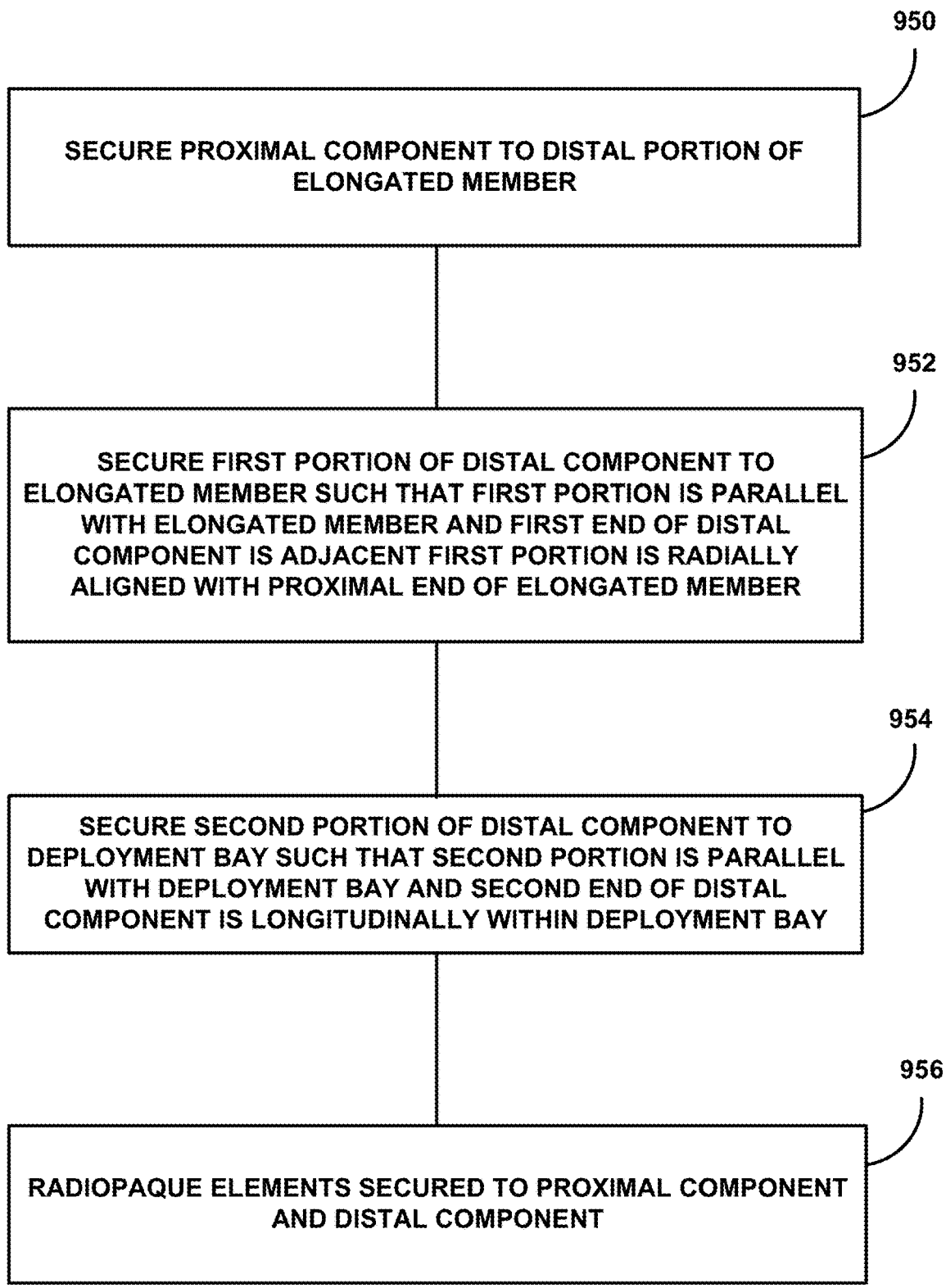
FIG. 16 depicts a flowchart of a method of making a delivery device for delivering a medical device to a target site within a patient using a delivery device.

FIG. 16 depicts a flowchart of a method of making a delivery device for delivering a medical device to a target site within a patient. The flowchart of FIG. 16 is discussed with reference to the delivery device of FIGS. 2A-5B. It is to be understood that the depicted order of steps of the method of FIG. 16 is depicted for purposes of illustration only, as in other examples the method may be completed in another order.

Proximal component 74 of compression mechanism 54 may be secured to elongated member 62 (950). Proximal component 74 may be secured to elongated member 62. For example, proximal component 74 may be chemically bonded, overmolded, heat bonded, or mechanically attached to elongated member 62. Inner lumen 81 of proximal component 74 may be secured to an outer surface of elongated member 62. In some examples, proximal component 74 may be secured to elongated member 62 at a location that is somewhat proximal to distal end 130 of elongated member 62.

Distal component 76 may connect elongated member 62 to deployment bay 52. Distal component 76 may be a flexible sheet with first end 116 and second end 120. First portion 126 of distal component 76 adjacent first end 116 may be secured to elongated member 62 (952). First portion 126 of distal component 76 may be secured to elongated member 62 such that first end 116 of distal component 76 is radially aligned with distal end 130 of elongated member 62 and first portion 126 extends proximally parallel with elongated member 62. First portion 126 may be chemically bonded to elongated member 62. First portion 126 may be secured to elongated member 62 at a location that is distal from the location at which proximal component 74 is secured to elongated member 62.

Second portion 128 of distal component 76 that is adjacent second end 120 of distal component is secured to deployment bay 52 (954). Second portion 128 of distal component 76 is secured to deployment bay 52 such that second portion 128 extends proximally from second end 120 in parallel with deployment bay 52. Second portion 128 may be chemically bonded, overmolded, heat bonded, or mechanically attached to deployment bay 52.

Radiopaque elements 90 may be secured to proximal component 74 and distal component 76 (956). For example, radiopaque element 90 of an outer band constructed of a radiopaque material may be secured to outer circumference of both proximal component 74 and distal component 76. In some examples, radiopaque elements 90 may be secured between an proximal interface of proximal component 74 and elongated member 62 and/or a distal interface between distal component 76 and deployment bay 52 to strength one or both interfaces.

This disclosure is primary directed to medical delivery devices that include one or more components that axially deform in predetermined ways in response to applied forces that are over predetermined thresholds to deliver an implantable medical device to a right atrium of a heart of a patient. However, one or more aspects of this disclosure may also be applicable to delivering other insertable or implantable medical devices to the right atrium or other areas of a patient. For one example, as discussed herein aspects of this disclosure may be applicable to delivering a lead that includes distal fixation elements to a target site within a patient. Other applications for aspects of this disclosure would also be understood by one of ordinary skill in the art.

Various examples have been described. These and other examples are within the scope of the following claims.

The invention claimed is:

1. A medical device delivery system comprising:
   an elongated member configured to navigate a vascular system of a patient;
   a deployment bay connected to a distal end of the elongated member and configured to house at least a portion of an insertable or implantable medical device, the deployment bay defining a distal opening configured for deployment of the insertable or implantable medical device out of the deployment bay at a target site in a patient; and
   a compression mechanism configured to longitudinally move the elongated member and a distal portion of the deployment bay toward each other in response to the deployment bay applying an above-threshold distal force against the target site, wherein:
   a distal planar surface of the deployment bay defines the distal opening;
   the target site defines a plane; and
   the compression mechanism is configured to axially deform relatively more on one side of a longitudinal axis of the medical device delivery system than on an opposing side of the longitudinal axis in response to the distal planar surface contacting the plane at an above-threshold angle.

2. The system of claim 1, wherein the compression mechanism is configured to axially compress to longitudinally move the elongated member and deployment bay toward each other.

3. The system of claim 1, wherein the angle is reduced as a result of the compression mechanism longitudinally deforming relatively more on one side of the longitudinal axis than on the opposing side.

4. The system of claim 1, wherein the elongated member, the compression mechanism, and the deployment bay are substantially symmetrical about a central plane of the system.

5. The system of claim 1, wherein the insertable or implantable medical device is a leadless pacemaker.

6. The system of claim 1, wherein the insertable or implantable medical device is configured to secure itself to the target site using one or more fixation elements at a distal end of the insertable or implantable medical device.

7. The system of claim 6, wherein the one or more fixation elements comprise one or more fixation tines.

8. The system of claim 1, further comprising a proximal radiopaque marker and a distal radiopaque marker, wherein the proximal radiopaque marker and the distal radiopaque marker are configured to longitudinally move toward each other in response to the compression mechanism moving the elongated member and the distal portion of the deployment bay longitudinally toward each other.

9. The system of claim 8, wherein the proximal radiopaque marker is near a proximal portion of the compression mechanism, and the distal radiopaque marker is near a distal portion of the compression mechanism.

10. The system of claim 1, wherein the above-threshold force is greater than a force required to insert the delivery system through an introducer sheath to gain access to the vascular system of the patient.

11. The system of claim 1, wherein the compression mechanism defines one or more compression lumens.

12. The system of claim 11, wherein the one or more compression lumens of the compression mechanism include a guidewire lumen that is configured to receive a guidewire.

13. The system of claim 12, wherein the one or more compression lumens of the compression mechanism include a medical device lumen that is configured to receive a portion of the insertable or implantable medical device.

14. The system of claim 13, further comprising:
   a hub at a proximal end of the elongated member; and
   a deployment mechanism configured to deploy the insertable or implantable medical device, wherein the one or more compression lumens of the compression mechanism include a deployment lumen that is configured to house at least a portion of the deployment mechanism.

15. The system of claim 1 wherein the elongated member defines one or more elongated member lumens.

16. The system of claim 15, wherein the compression mechanism defines one or more compression lumens, wherein the one or more compression lumens of the compression mechanism include a first guidewire lumen that is configured to receive a guidewire, and wherein the one or more elongated member lumens of the elongated member include a second guidewire lumen that is configured to receive the guidewire.

17. The system of claim 16, wherein the first guidewire lumen of the compression mechanism is coaxial with the second guidewire lumen of the elongated member.

18. The system of claim 16, wherein the one or more compression lumens of the compression mechanism include a first medical device lumen that is configured to receive a first portion of the insertable or implantable medical device, and wherein the one or more elongated member lumens of the elongated member include a second medical device lumen that is configured to receive a second portion of the insertable or implantable medical device.

19. The system of claim 18, wherein the first medical device lumen of the compression mechanism is coaxial with the second medical device lumen of the elongated member.

20. The system of claim 15, further comprising:
a hub at a proximal end of the elongated member; and
a deployment mechanism configured to deploy the insertable or implantable medical device, wherein the compression mechanism defines one or more compression lumens, wherein the one or more compression lumens of the compression mechanism include a first deployment lumen that is configured to house at least a first portion of the deployment mechanism, and wherein the one or more elongated member lumens of the elongated member include a second deployment lumen that is configured to house at least a second portion of the deployment mechanism.

21. The system of claim 20, wherein the first deployment lumen of the compression mechanism is coaxial with the second deployment lumen of the elongated member.

22. The system of claim 1, further comprising one or more deflection members longitudinally embedded within the elongated member and configured to deflect the elongated member in a predetermined manner when the delivery device is inserted in the patient.

23. The system of claim 1, wherein the compression mechanism is configured to longitudinally move the elongated member and the distal portion of the deployment bay toward each other by transitioning from a predetermined uncompressed state to a predetermined compressed state in response to the deployment bay applying the above-threshold distal force against the target site.

24. The system of claim 23, wherein the compression mechanism is configured to longitudinally move the elongated member and the deployment bay away from each other by transitioning from the predetermined compressed state to the predetermined uncompressed state in response to the deployment bay ceasing the application of the distal force against the target site.

25. The system of claim 1, wherein the compression mechanism is located immediately proximal to the deployment bay.

26. The system of claim 25, wherein the compression mechanism is located immediately distal to the elongated member.

27. The system of claim 1, wherein the compression mechanism comprises:
a distal component that is configured to deform in response to the deployment bay applying the distal force; and
a proximal component that is configured to move longitudinally toward the distal component in response to the distal component deforming.

28. The system of claim 27, wherein the proximal component is configured to remain substantially undeformed in response to the deployment bay applying the distal force.

29. The system of claim 1, wherein the compression mechanism comprises:
a distal component that defines a flexed sheet with a first end and a second end, wherein a proximal portion of the distal component that is adjacent the first end is secured to a distal portion of the elongated member such that the first end is substantially longitudinally aligned with a distal end of the elongated member, and wherein a distal portion of the distal component that is adjacent the second end is secured to a proximal portion of the deployment bay such that the second end is distal the distal portion of the distal component; and
a proximal component secured to a length of the elongated member that is proximal to the distal portion of the elongated member, the proximal component defining a first radius that is larger than a radius of the elongated member and a second radius that is smaller than a radius of the deployment bay, the proximal component extending radially outward from the first radius to the second radius as the proximal component extends longitudinally in a distal direction.

30. The system of claim 29, wherein the proximal component is less flexible than the distal component.

31. The system of claim 1, wherein the compression mechanism defines a tubular wall that is secured to longitudinally adjacent portions of the system and is made of a first material that is more compressible material than a second material of the longitudinally adjacent portions of the system.

32. The system of claim 1, wherein the compression mechanism defines a tubular wall that connects to longitudinally adjacent portions of the system and defines a thinner radial wall width than the longitudinally adjacent portions of the system.

33. The system of claim 1, wherein the compression mechanism includes an accordion structure that is secured to longitudinally adjacent portions of the system and defines panels that alternate angling radially in towards and angling radially out away from a longitudinal axis of the compression mechanism along a longitudinal length of the compression mechanism.

34. A medical device delivery system comprising:
an elongated member configured to navigate a vascular system of a patient;
a deployment bay connected to a distal end of the elongated member and configured to house at least a portion of an insertable or implantable medical device, the deployment bay defining a distal opening configured for deployment of the insertable or implantable medical device out of the deployment bay at a target site in a patient; and
a compression mechanism configured to longitudinally move the elongated member and a distal portion of the deployment bay toward each other in response to the deployment bay applying an above-threshold distal force against the target site, wherein the compression mechanism includes a plurality of interlocking components, the plurality of interlocking components comprising a first interlocking component that is secured to a distal portion of the elongated member and a second interlocking component that is secured to a proximal portion of the deployment bay, wherein the plurality of interlocking components slidably couples the first interlocking component to the second interlocking component such that the first interlocking component is configured to longitudinally slide relative to the second interlocking component in response to the distal force.

35. A medical device delivery system comprising:
an elongated member configured to navigate a vascular system of a patient;
a deployment bay connected to a distal end of the elongated member and configured to house at least a portion of an insertable or implantable medical device, the deployment bay defining a distal opening for deployment of the insertable or implantable medical device out of the deployment bay at a target site in a patient;
a hub at a proximal end of the elongated member configured to navigate the system and deploy the insertable or implantable medical device; and
a compression mechanism configured to longitudinally move the elongated member and a distal portion of the deployment bay toward each other in response to the deployment bay applying an above-threshold distal force against the target site, the compression mechanism comprising:
a distal component that defines a flexed sheet with a first end and a second end, wherein a proximal portion of the distal component that is adjacent the first end is secured to a distal portion of the elongated member such that the first end is substantially longitudinally aligned with a distal end of the elongated member, and wherein a distal portion of the distal component that is adjacent the second end is secured to a proximal portion of the deployment bay such that the second end is distal the distal portion of the distal component; and
a proximal component secured to a length of the elongated member that is proximal to the distal portion of the elongated member, the proximal component defining a first radius that is larger than a radius of the elongated member and a second radius that is smaller than a radius of the deployment bay, the proximal component extending radially outward from the first radius to the second radius as the proximal component extends longitudinally in a distal direction.

\* \* \* \* \*